US012600758B2

(12) United States Patent
Bates et al.

(10) Patent No.: US 12,600,758 B2
(45) Date of Patent: Apr. 14, 2026

(54) INTERLEUKIN-2 MUTEINS FOR THE EXPANSION OF T-REGULATORY CELLS

(71) Applicant: AMGEN INC., Thousand Oaks, CA (US)

(72) Inventors: Darren L. Bates, Oak Park, CA (US); Sue J. Sohn, Daly City, CA (US); Hannah Beth Catterall, Santa Monica, CA (US); Zhulun Wang, Los Altos, CA (US)

(73) Assignee: AMGEN INC., Thousand Oaks, CA (US)

( * ) Notice: Subject to any disclaimer, the term of this patent is extended or adjusted under 35 U.S.C. 154(b) by 1097 days.

(21) Appl. No.: 17/634,685

(22) PCT Filed: Aug. 13, 2020

(86) PCT No.: PCT/US2020/046202
§ 371 (c)(1),
(2) Date: Feb. 11, 2022

(87) PCT Pub. No.: WO2021/030602
PCT Pub. Date: Feb. 18, 2021

(65) Prior Publication Data
US 2022/0289807 A1 Sep. 15, 2022

Related U.S. Application Data

(60) Provisional application No. 62/886,283, filed on Aug. 13, 2019.

(51) Int. Cl.
| | |
|---|---|
| *C07K 14/55* | (2006.01) |
| *A61K 38/20* | (2006.01) |
| *A61P 3/10* | (2006.01) |
| *A61P 37/06* | (2006.01) |
| *A61P 19/02* | (2006.01) |

(52) U.S. Cl.
CPC .......... *C07K 14/55* (2013.01); *A61K 38/2013* (2013.01); *A61P 3/10* (2018.01); *A61P 37/06* (2018.01); *A61P 19/02* (2018.01)

(58) Field of Classification Search
CPC ................ C07K 14/55; A61K 38/2013; A61K 47/6813; C12N 5/0637
See application file for complete search history.

(56) References Cited

U.S. PATENT DOCUMENTS

| | | | |
|---|---|---|---|
| 3,691,016 | A | 9/1972 | Patel |
| 3,773,919 | A | 11/1973 | Boswell |
| 3,969,287 | A | 7/1976 | Jaworek |
| 4,179,337 | A | 12/1979 | Davis |
| 4,195,128 | A | 3/1980 | Hildebrand |
| 4,229,537 | A | 10/1980 | Hodgins |
| 4,247,642 | A | 1/1981 | Hirohara |
| 4,301,144 | A | 11/1981 | Iwashita |

| | | | |
|---|---|---|---|
| 4,330,440 | A | 5/1982 | Ayers |
| 4,439,196 | A | 3/1984 | Higuchi |
| 4,447,224 | A | 5/1984 | Decant, Jr. |
| 4,447,233 | A | 5/1984 | Mayfield |
| 4,475,196 | A | 10/1984 | La Zor |
| 4,486,194 | A | 12/1984 | Ferrara |
| 4,487,603 | A | 12/1984 | Harris |
| 4,496,689 | A | 1/1985 | Mitra |
| 4,596,556 | A | 6/1986 | Morrow |
| 4,640,835 | A | 2/1987 | Shimizu |
| 4,670,417 | A | 6/1987 | Iwasaki |
| 4,790,824 | A | 12/1988 | Morrow |
| 4,791,192 | A | 12/1988 | Nakagawa |
| 4,941,880 | A | 7/1990 | Burns |
| 4,968,607 | A | 11/1990 | Dower |
| 5,064,413 | A | 11/1991 | McKinnon |
| 5,312,335 | A | 5/1994 | McKinnon |
| 5,383,851 | A | 1/1995 | McKinnon, Jr. |
| 5,399,163 | A | 3/1995 | Peterson |
| 5,677,425 | A | 10/1997 | Bodmer |
| 6,037,525 | A | 3/2000 | Thompson |
| 6,177,612 | B1 | 1/2001 | Jordan |
| 6,239,328 | B1 | 5/2001 | Thompson |
| 6,245,974 | B1 | 6/2001 | Michalowski |
| 6,348,192 | B1 | 2/2002 | Chan |
| 6,388,066 | B1 | 5/2002 | Bruce |
| 6,737,056 | B1 | 5/2004 | Presta |
| 6,927,043 | B2 | 8/2005 | Chan |
| 6,955,807 | B1 | 10/2005 | Shanafelt |
| 7,091,321 | B2 | 8/2006 | Gillies |
| 7,105,653 | B2 | 9/2006 | Shanafelt |
| 7,129,062 | B2 | 10/2006 | Mermod |

(Continued)

FOREIGN PATENT DOCUMENTS

| | | |
|---|---|---|
| DE | 102008023820 A1 | 11/2009 |
| EP | 0200133 A | 1/1979 |

(Continued)

OTHER PUBLICATIONS

Lan et al., "The regulatory, inflammatory, and T cell programming roles of interleukin-2 (IL-2)," J Autoimmun 31:7-12, 2008.

Laurent et al., T-cell activation by treatment of cancer patients with EMD 521873 (Selectikine), an IL-2/anti-DNA fusion protein, Jan. 2013, vol. 11, 5.

Leder et al., "Consequences of widespread deregulation of the c-myc gene in transgenic mice: multiple neoplasms and normal development," Cell, 45:485-495 (1986).

Liu et al., "Engineered Interleukin-2 Antagonists for the Inhibition of Regulatory T Cells", J Immunother., vol. 32 (9), pp. 887-894 (2009).

(Continued)

*Primary Examiner* — Gyan Chandra
(74) *Attorney, Agent, or Firm* — David Roadcap

(57) ABSTRACT

Provided herein are IL-2 muteins and IL-2 mutein Fc fusion molecules that preferentially expand and activate cells and are amenable to large scale production. Also provided herein are methods of making and using the compositions of the present invention.

25 Claims, 3 Drawing Sheets

Specification includes a Sequence Listing.

(56) References Cited

U.S. PATENT DOCUMENTS

| 7,259,010 | B2 | 8/2007 | Kim |
| 7,317,091 | B2 | 1/2008 | Lazar |
| 7,326,567 | B2 | 2/2008 | Saha |
| 7,371,371 | B2 | 5/2008 | Epstein |
| 7,422,874 | B2 | 9/2008 | Kim |
| 7,507,406 | B2 | 3/2009 | Gillies |
| 7,514,073 | B2 | 4/2009 | Epstein |
| 7,569,215 | B2 | 8/2009 | Wittrup |
| 7,695,963 | B2 | 4/2010 | Agulnick |
| 7,790,415 | B2 | 9/2010 | Gillies |
| 7,803,361 | B2 | 9/2010 | Epstein |
| 7,888,071 | B2 | 2/2011 | Gillies |
| 8,124,066 | B2 | 2/2012 | Epstein |
| 8,592,562 | B2 | 11/2013 | Kannan |
| 2006/0269515 | A1 | 11/2006 | Denis-Mize |
| 2007/0161087 | A1 | 7/2007 | Glaesner |
| 2009/0171562 | A1 | 7/2009 | Shimada |
| 2010/0286374 | A1 | 11/2010 | Kannan |
| 2011/0091412 | A1 | 4/2011 | Wittrup et al. |
| 2011/0150826 | A1 | 6/2011 | Paulsen |
| 2011/0274650 | A1 | 11/2011 | Gavin |
| 2013/0011401 | A1 | 1/2013 | Huber |
| 2014/0286898 | A1 | 9/2014 | Gavin et al. |
| 2015/0218260 | A1 | 8/2015 | La Roche |
| 2018/0228842 | A1 | 8/2018 | Kenan |

FOREIGN PATENT DOCUMENTS

| EP | 0088046 B1 | 12/1987 |
| EP | 0143949 B1 | 10/1988 |
| EP | 0036676 B2 | 9/1990 |
| EP | 506124 A | 9/1992 |
| EP | 0460846 B1 | 2/2002 |
| EP | 0058481 B2 | 5/2003 |
| EP | 1252192 B1 | 8/2006 |
| EP | 2288372 B1 | 2/2012 |
| WO | 1987005330 A1 | 9/1987 |
| WO | 1988007054 A1 | 9/1988 |
| WO | 1990000565 A1 | 1/1990 |
| WO | 1993015722 A1 | 8/1993 |
| WO | 1999060128 A1 | 11/1999 |
| WO | 2002046227 A2 | 6/2002 |
| WO | 2003086444 A1 | 10/2003 |
| WO | 2004082681 A1 | 9/2004 |
| WO | 2004099249 A2 | 11/2004 |
| WO | 2005000892 A2 | 1/2005 |
| WO | 2005086751 A2 | 9/2005 |
| WO | 2005086798 A2 | 9/2005 |
| WO | 2006034488 A2 | 3/2006 |
| WO | 2006138181 A2 | 12/2006 |
| WO | 2007095643 A2 | 8/2007 |
| WO | 2007100770 A2 | 9/2007 |
| WO | 2008062158 A2 | 5/2008 |
| WO | 2008106116 A2 | 9/2008 |
| WO | 2008112325 A2 | 9/2008 |
| WO | 2009061853 A2 | 5/2009 |
| WO | 2009089004 A1 | 7/2009 |
| WO | 2009135615 A2 | 11/2009 |
| WO | 2010017220 A1 | 2/2010 |
| WO | 2010085495 A1 | 7/2010 |
| WO | 2011063348 A1 | 5/2011 |
| WO | 2011076781 A1 | 6/2011 |
| WO | 2012075037 A1 | 6/2012 |
| WO | 2012123381 A1 | 9/2012 |
| WO | 2012125850 A1 | 9/2012 |
| WO | 2013093809 A1 | 6/2013 |
| WO | 2013119716 A1 | 8/2013 |
| WO | 2013177062 A2 | 11/2013 |
| WO | 2014145016 A2 | 9/2014 |
| WO | 2014153063 A1 | 9/2014 |
| WO | 2014153111 A2 | 9/2014 |
| WO | 2016014428 A2 | 1/2016 |
| WO | 2016025385 A1 | 2/2016 |
| WO | 2016164937 A2 | 10/2016 |
| WO | 2017044464 A1 | 3/2017 |
| WO | 2018217989 | 11/2018 |
| WO | 2020046202 | 3/2020 |
| WO | 2021030602 | 2/2021 |
| WO | 2021127262 A1 | 6/2021 |

OTHER PUBLICATIONS

Luckow and Summers, Trends in the Development ofBaculovirus Expression Vectors, Bio/Technology (1988), 6(1):47-55.

MacDonald, "Expression of the pancreatic elastase I gene in transgenic mice", Hepatology, vol. 7 (Suppl 1), pp. 42S-51S (1987).

Magram et al., "Developmental regulation of a cloned adult beta-globin gene in transgenic mice" Nature, 315:338-340 (1985).

Malek, "The biology of interleukin-2," Annu Rev Immunol 26:453-479, 2008.

Margolin et al., Phase I trial of BAY 50-4798, an interleukin-2-specific agonist in advanced melanoma and renal cancer, Jun. 2007, Clin. Cancer Res, vol. 13(11), 3312-9.

Mason et al., "The hypogonadal mouse: reproductive functions restored by gene therapy", Science, vol. 234 (4782), pp. 1372-1378 (1986).

Matthews et al., BAY 50-4798, a novel, high-affinity receptor-specific recombinant interleukin-2 analog, induces dose-dependent increases in CD25 expression and proliferation among unstimulated, human peripheral blood mononuclear cells in vitro, Dec. 2004, Clin. Immunol., vol. 113(3); 248-55.

McMahan et al., "A novel IL-1 receptor, cloned from B cells by mammalian expression, is expressed in many cell types", EMBO J., vol. 10 (10), pp. 2821-2832 (1991).

Nagase et al., "Despite increased CD4+Foxp3+ cells within the infection site, BALB/c IL-4 receptor-deficient mice reveal CD4+ Foxp3-negative T cells as a source of IL-10 in Leishmania major susceptibility," J Immunol 179:2435-2444, 2007.

Needleman et al., "A general method applicable to the search for similarities in the amino acid sequence of two proteins", J. Mol. Biol., vol. 48 (3), pp. 443-453 (1970).

Passerini et al., "STAT5-signaling cytokines regulate the expression of FOXP3 in CD4+CD25+ regulatory T cells and CD4+CD25- effector T cells", International Immunology, vol. 20 (3), pp. 421-431 (2008).

Pearson and Lipman, "Improved tools for biological sequence comparison", Proc. Natl. Acad. Sci. USA, vol. 85, pp. 2444-2448 (1988).

Peterson et al., "A long-lived IL-2 mutein that selectively activates and expands regulatory T cells as a therapy for autoimmune disease," Journal of Autoimmunity, 95:1-14 (2018).

Pinkert et al., "An albumin enhancer located 10 kb upstream functions along with its promoter to direct efficient, liver-specific expression in transgenic mice", Genes Dev., vol. 1 (3), pp. 268-276 (1987).

Randolph et al., "Surfactant-Protein interactions," Pharmaceutical Biotechnology 13:159-175 (2002).

Rao et al., "High-affinity CD25-binding IL-2 mutants potently stimulate persistent T cell growth," Biochemistry 44:10696-10701, 2005.

Readhead et al., "Expression of a myelin basic protein gene in transgenic shiverer mice: correction of the dysmyelinating phenotype", Cell, vol. 48 (4), pp. 703-712 (1987).

Rojas et al., "Deciphering the Molecular Bases of the Biological Effects of Antibodies Against Interleukin-2: a Versatile Platform for Fine Epitope Mapping", Immunobiology (2013), 218(1):105-113.

Saiki et al., Primer-Directed Enzymatic Amplification of DNA with a Thermostable DNA Polymerase, Science (1988) 239:487-491.

Sasaoki et al., "Deamidation at asparagine-88 in recombinant human interleukin 2," Chem Pharm Bull 40(4):976-980, 1992.

Sehouli et al., Epigenetic quantification of tumor-infiltrating T-lymphocytes, Epigenetics (2011), 6(2):236-246.

Shanafelt et al., "A T-cell selective interleukin 2 mutein exhibits potent antitumor activity and is well tolerated in vivo," Nat Biotechnol 18:1197-1202, 2000.

Shani, "Tissue-specific expression of rat myosin light-chain 2 gene in transgenic mice," Nature, vol. 314 (6008), pp. 283-286 (1985).

(56)                References Cited

OTHER PUBLICATIONS

Sidman et al., "Controlled release of macromolecules and pharmaceuticals from synthetic polypeptides based on glutamic acid," Biopolymers, vol. 22 (1), pp. 547-556 (1983).

Siegmund et al., "Unique phenotype of human tonsillar and in vitro-induced FOXP3+CD8+ T cells", J Immunol., vol. 182 (4), pp. 2124-2130 (2009).

Smith and Waterman., "Comparison of Biosequences", Advances in Applied Mathematics 2, pp. 482-489 (1981).

Sojar and Bahl, "A Chemical Method for the Deglycosylation of Proteins", Arch. Biochem. Biophys., vol. 259 (1), pp. 52-57 (1987).

Stauber et al., "Crystal structure of the IL-2 signaling complex: Paradigm for a heterotrimeric cytokine receptor", Proc Natl Acad Sci USA, vol. 103 (8), pp. 2788-2793 (2006).

Steppan et al., Reduced secondary cytokine induction by BAY 50-4798, a high-affinity receptor-specific interleukin-2 analog, Mar. 2006, J. Interferon Cytokine Res., vol. 26(3); 171-8.

Stork et al., "N-Glycosylation as Novel Strategy to Improve Pharmacokinetic Properties of Bispecific Single-chain Diabodies", J Biol Chem., vol. 283 (12), pp. 7804-7812 (2008).

Strohl, Optimization of Fc-mediated effector functions of monoclonal antibodies, Review Curr Opin Biotechnol, Dec. 2009;20(6):685-91. doi: 10.1016/j.copbio.2009.10.011. Epub Nov. 4, 2009.

Swift et al., "Tissue-Specific Expression of the Rat Pancreatic Elastase I Gene in Transgenic Mice", Cell, vol. 38 (3), pp. 639-646 (1984).

Tang et al., "Central role of defective interleukin-2 production in the triggering of islet autoimmune destruction," Immunity 28:687-697, 2008.

Thanos et al., "Hot-Spot mimicry of a cytokine receptor by a small molecule", PNAS, 103(42):15422-15427, 2006.

Thornsen, D. R. et al., "Promoter-regulatory region of the major immediate early gene of human cytomegalovirus," Proc. Natl. Acad. U.S.A., 81:659-663 (1984).

Thotakura and Bahl, "Enzymatic Deglycosylation of Glycoproteins", Meth. Enzymol., vol. 138, pp. 350-359 (1987).

Villa-Komaroff et al., "A bacterial clone synthesizing proinsulin", Proc Natl Acad Sci U S A., vol. 75 (8), pp. 3727-3731 (1978).

Wagner et al., "Nucleotide sequence of the thymidine kinase gene of herpes simplex virus type 1," Proc Natl Acad Sci U S A., vol. 78 (3), pp. 1441-1445 (1981).

Wang et al., "Structure of the quaternary complex of interleukin-2 with its α, β, and γ c receptors," Science 310:1159-1163, 2005.

Wozniak-Knopp et al., "Stabilisation of the Fc Fragment of Human IgG1 by Engineered Intradomain Disulfide Bonds," PLoS One, vol. 7 (1), pp. 1-11 (2012).

Written Opinion of PCT/US2020/046202, Feb. 18, 2021.

Written Opinion of the International Searching Authority, International Application No. PCT/US2016/030843, Dec. 8, 2016.

Yamamoto et al., "Identification of a Functional Promoter in the Long Terminal Repeat of Rous Sarcoma Virus", Cell, vol. 22 (3), pp. 787-797 (1980).

Extended European Search Report issued to European Application No. 24168750.8, dated Aug. 9, 2024.

Adams et al., "The c-myc Oncogene Driven by Immunoglobulin Enhancers Induces Lymphoid Malignancy in Transgenic Mice", Nature, vol. 318, pp. 533-538 (Dec. 1985).

Aldrich et al., EASE Vectors for Rapid Stable Expression of Recombinant Antibodies, Biotechnol. Prog. (2003), 19:1443-1438.

Alexander et al., "Expression of the c-myc Oncogene Under Control of an Immunoglobulin Enhancer in Emu-myc Transgenic Mice", Molecular and Cellular Biology, vol. 7 (4), pp. 1436-1444 (Apr. 1987).

Altschul and Gish, "Local Alignment Statistics", Meth. Enzymol., vol. 266, pp. 460-480 (1996).

Altschul et al., "Basic Local Alignment Search Tool", J. Mol. Biol., vol. 215 (3), pp. 403-410 (1990).

Altschul et al., "Gapped BLAST and PSI-BLAST: a new generation of protein database search programs", Nucleic Acids Res., vol. 25 (17), pp. 3389-3402 (1997).

Arakawa et al., "Protein-Solvent Interactions in Pharmaceutical Formulations", Pharm. Res., vol. 8 (3), pp. 285-291 (1991).

Banks et al., Integrated Modeling Program, Applied Chemical Theory (IMPACT), J. Comp. Chem. (2005), 26: 1752-1780.

Benoist et al., "In Vivo Sequence Requirements of the SV40 Early Promoter Region", Nature, vol. 290, pp. 304-310 (Mar. 26, 1981).

Bluestone et al., IL-2: Change Structure . . . Change Function, Immunity (2015), 42:779-781.

Boyman et al., "Selective Stimulation of T Cell Subsets with Antibody-Cytokine Immune Complexes", Science, 311:1924-1927, 2006.

Collins et al., "Identification of specific residues of human interleukin 2 that affect binding to the 70-kDa subunit (p70) of the interleukin 2 receptor", Proc. Natl. Acad. Sci. USA, 85:7709-7713, 1988.

Cosman et al., "Cloning, Sequence and Expression of Human Interleukin-2 Receptor", Nature, vol. 312 (5996), pp. 768-771 (1984).

Creighton, "Proteins: Structure and Molecular Properties," 2nd ed., W. H. Freeman and Company, N.Y. (1984) (Table of Contents Only).

De Boer et al., "The tac promoter: a functional hybrid derived from the trp and lac promoters", Proc. Natl. Acad. Sci. USA, vol. 80 (1), pp. 21-25 (1983).

Devereux et al., A Comprehensive Set of Sequence Analysis Programs for the VAX, Nucl. Acid Res. (1984), 12(1):387-395.

Du et al., "Improved Folding Yields of a Model Protein Using Protein Disulfide Isomerase", Pharmaceutical Research, vol. 15 (12), pp. 1808-1815 (1998).

Edge et al., "Deglycosylation of Glycoproteins by Trifluoromethanesulfonic Acid", Anal. Biochem., vol. 118, pp. 131-137 (1981).

Fell et al., Genetic construction and characterization of a fusion protein consisting of a chimeric F(ab') with specificity for carcinomas and human IL-2, Apr. 1991, J. Immunol, vol. 146(7); 2446-52.

Finkelman et al., "Anti-Cytokine Antibodies as Carrier Proteins", J. Immunol. 151(3):1235-1244, 1993.

Fujii et al., "Activation of Stat5 by interleukin 2 requires a carboxyl-terminal region of the interleukin 2 receptor beta chain but is not essential for the proliferative signal transmission," PNAS 92:5482 5486, 1995.

Gillessen et al., A phase I dose-escalation study of the immunocytokine EMD 521873 (Selectikine) in patients with advanced solid tumours, Jan. 2013, Eur J Cancer, vol. 49(1); 35-44.

Gillies et al. Biological activity and in vivo clearance of antitumor antibody/cytokine fusion proteins, May/Jun. 1993, Bioconjug Chem, vol. 4(3); 230-5.

Gillies et al., A low-toxicity IL-2-based immunocytokine retains antitumor activity despite its high degree of IL-2 receptor selectivity, Jun. 2011, Clin. Cancer Res., vol. 17(11); 3673-85.

Gillies et al., Antibody-targeted interleukin 2 stimulates T-cell killing of autologous tumor cells, Feb. 1992, Proc Natl Acad Sci U.S.A., vol. 89(4); 1428-32.

Gillies et al., Improved circulating half-life and efficacy of an antibody-interleukin 2 immunocytokine based on reduced intracellular proteolysis, Jan. 2002, Clin. Cancer Res, vol. 8(1); 210-6.

Gluzman, Yakov, "SV40-Transformed Simian Cells Support the Replication of Early SV40 Mutants", Cell, vol. 23, pp. 175-182 (1981).

Grosschedel et al., Introduction of au Immunoglobulin Gene into the Mouse Germ Line: Specific Expression in Lymphoid Cells and Synthesis of Functional Antibody, Cell (1984), 38(3):647-658.

Hammer et al., "Diversity of Alpha-Fetoprotein Gene Expression in Mice Is Generated by a Combination of Separate Enhancer Elements", Science, vol. 235 (4784), pp. 53-58 (1987).

Hanahan, "Heritable formation of pancreatic beta-cell tumours in transgenic mice expressing recombinant insulin/simian virus 40 oncogenes", Nature, vol. 315 (6015), pp. 115-122 (1985).

Hartmann, Gunther, "Technology evaluation: BAY-50-4798, Bayer", Current Opinion in Molecular Therapeutics, 6(2):221-227 + 684, 2004.

Higgins and Sharp, "Fast and sensitive multiple sequence alignments on a microcomputer", Cabios Comm., vol. 5 (2), pp. 151-153 (1989).

(56)         References Cited

OTHER PUBLICATIONS

Hristodorov et al., "With or Without Sugar? (A)glycosylation of Therapeutic Antibodies", Mol Biotechnol, vol. 54 (3), pp. 1056-1068 (2013).

Innis et al., PCR Protocols—A Guide to Methods and Applications, Polymerase Chain Reaction (Current Communications in Molecular Biology), Academic Press, Inc. (1990), 6(7):229.

International Preliminary Report on Patentability and Written Opinion issued to PCT/US2020/046202, dated Feb. 8, 2022.

International Preliminary Report on Patentability, International Application No. PCT/US2016/030843, dated Oct. 19, 2017.

International Search Report for International Application No. PCT/US2016/030843, Dec. 12, 2016.

International Search Report issued to PCT/US2020/046202, Nov. 5, 2020.

Jung et al., Aglycosylated IgG variants expressed in bacteria that selectively bind FcγRI potentiate tumor cell killing by monocyte-dendritic cells, Jan. 12, 2010, PNAS, vol. 107, 604-609.

Karlin et al., "Applications and statistics for multiple high-scoring segments in molecular sequences", Proc. Natl. Acad. Sci. USA, vol. 90 (12), pp. 5873-5877 (1993).

Kelsey et al., "Species- and tissue-specific expression of human alpha 1-antitrypsin in transgenic mice", Genes Dev., vol. 1 (2), pp. 161-171 (1987).

Kendra et al., Pharmacokinetics and stability of the ch14.18-interleukin-2 fusion protein in mice, Aug. 1999, Cancer Immunol Immunother, vol. 48(5), 219-29.

Kendrick et al., "Physical Stabilization of Proteins in Aqueous Solution", Rationale Design of stable protein formulations-theory and practice, Eds. Carpenter and Manning, Kluwer Academic/Plenum Publishers, New York, pp. 61-84 (2002).

King et al., Phase I clinical trial of the immunocytokine EMD 273063 in melanoma patients, Nov. 2004, J. Clin. Oncol., vol. 22(22); 4463-73.

Ko et al., Safety, pharmacokinetics, and biological pharmacodynamics of the immunocytokine EMD 273066 (huKS-IL2): results of a phase I trial in patients with prostate cancer, May/Jun. 2004, J Immunother, vol. 27(3); 233-239.

Kollias et al., "Regulated expression of human A gamma-, beta-, and hybrid gamma beta-globin genes in transgenic mice: manipulation of the developmental expression patterns", Cell, vol. 46 (1), pp. 89-94 (1986).

Koreth et al., "Interleukin-2 and Regulatory T Cells in Graft-versus-Host Disease", The New England Journal of Medicine, 365(22):2055-2066, 2011.

Krumlauf et al., "Developmental regulation of alpha-fetoprotein genes in transgenic mice", Mol Cell Biol., vol. 5 (7), pp. 1639-1648 (1985).

Search Report issued to Singapore Application No. 11202201328T, dated Oct. 22, 2024.

Search Report issued to Taiwan application No. 109127567, dated Oct. 4, 2024.

10-day 40°C
Stability % MP
SEC

A

B

C

D

INTERLEUKIN-2 MUTEINS FOR THE EXPANSION OF T-REGULATORY CELLS

CROSS-REFERENCE TO RELATED APPLICATIONS

This application is a National Stage application under 35 U.S.C. § 371 of International Application No. PCT/US2020/046202, having an international filing date of Aug. 13, 2020, which claims the benefit of U.S. Provisional Patent Application No. 62/886,283, filed Aug. 13, 2019, all of which are incorporated herein by reference in their entirety for all purposes.

BACKGROUND

IL-2 binds three transmembrane receptor subunits: IL-2Rβ and IL-2Rγ which together activate intracellular signaling events upon IL-2 binding, and CD25 (IL-2Rα) which serves to stabilize the interaction between IL-2 and IL-2Rβγ. The signals delivered by IL-2Rβγ include those of the PI3-kinase, Ras-MAP-kinase, and STAT5 pathways.

T cells require expression of CD25 to respond to the low concentrations of IL-2 that typically exist in tissues. T cells that express CD25 include both FOXP3+ regulatory T cells (Treg cells), which are essential for suppressing autoimmune inflammation, and FOXP3− T cells that have been activated to express CD25. FOXP3− CD25+ T effector cells (Teff) may be either CD4+ or CD8+ cells, both of which may contribute to inflammation, autoimmunity, organ graft rejection, or graft-versus-host disease. IL-2-stimulated STAT5 signaling is crucial for normal T-reg cell growth and survival and for high FOXP3 expression.

In co-owned WO 2010/085495, we describe the use of IL-2 muteins to preferentially expand or stimulate Treg cells. When administered to a subject, the effect on Treg cells is useful for treating inflammatory and autoimmune diseases. Although the IL-2 muteins described therein are useful for expanding Treg over Teff cells in vivo, it was desirable to create IL-2 muteins that had optimal attributes for a human therapeutic.

SUMMARY

Described herein are IL-2 muteins that are amenable to high-yield manufacturability and have pharmacological activity. In particular, IL-2 muteins of the present invention have an improved Treg:Teff selectivity window. In the effort to produce such molecules for use as human therapeutics, a number of unexpected and unpredictable observations occurred. The compositions and methods described herein resulted from that effort.

The IL-2 muteins described herein have a relatively low likelihood of creating an immune response against the IL-2 mutein and/or endogenous IL-2 and provide Treg preferential expansion and activation. Moreover, in certain embodiments, the IL-2 mutein is fused to a molecule, e.g. an antibody Fc, that increases the serum half-life when administered to a subject. IL-2 muteins have a short serum half-life (3 to 5 hrs for sub-cutaneous injection). Exemplary IL-2 mutein Fc fusions described herein have a half-life in humans of at least 1 day, at least 3 days, at least 5 days, at least 10 days, at least 15 days, at least 20 days, or at least 25 days. This effect on the pharmacokinetics of the IL-2 muteins allows for decreased or less frequent dosing of the IL-2 mutein therapeutic.

Moreover, when creating a pharmaceutical large molecule, consideration must be made for the ability to produce the large molecule in large quantities, while minimizing aggregation and maximizing the stability of the molecule. The IL-2 mutein Fc-fusion molecules demonstrate such attributes.

Additionally, in certain embodiments, the IL-2 mutein Fc-fusion protein contains an IgG1 Fc region. When it is desirable to abolish the effector functions of IgG1 (e.g., ADCC activity), it was found that mutation of the asparagine at position 297 to glycine (N297G; EU numbering scheme) provided greatly improved purification efficiency and biophysical properties over other mutations that lead to an aglycosylation IgG1 Fc. In preferred embodiments, cysteines are engineered into the Fc to allow disulfide bonds, which increased stability of the aglycosylated Fc-containing molecule. The usefulness of the aglycosylated Fc goes beyond the IL-2 mutein Fc-fusion context. Thus, provided herein are Fc-containing molecules, Fc-fusions and antibodies, comprising a N297G substitution and optionally substitution of one or more additional residues to cysteine.

In one aspect, the present invention provides a human interleukin-2 (IL-2) mutein comprising an amino acid sequence that is at least 90% identical to the amino acid sequence set forth in SEQ ID NO:1, wherein said IL-2 mutein has at least one mutation selected from V91K, D20L; D84R, E61Q; V91K, D20A, E61Q, M104T; N88K, M104L; V91H, M104L; V91K, H16E, M104V; V91K, H16R, M104V; V91K, H16R, M104T; V91K, D20A, M104T; V91K, H16E, M104T; V91K, H16E, E61Q, M104T; V91K, H16R, E61Q, M104T; V91K, H16E; V91H, D20A, M104T; H16E, V91H, M104V; V91H, D20A, E61Q, M104T; V91H, H16R, E16Q; V91K, D20A, M104V; H16E, V91H; V91H, D20A, M104V; H16E, V91H, M104T; H16E, V91H, E61Q, M104T; V91K, E61Q, H16E; V91K, H16R, M104L; H16E, V91H, E16Q; V91K, E61Q, H16R; D20W, V91K, E61Q; V91H, H16R; V91K, H16R; D20W, V91K, E61Q, M104T; V91K, D20A; V91H, D20A, E16Q; V91K, D20A, M104L; V91H, D20A; V91K, E61Q, D20A; V91H, M104T; V91H, M104V; V91K, E61Q; V91K, N88K, E61Q, M104T; V91K, N88K, E61Q; V91H, E61Q; V91K, N88K; D20A, H16E, M104T; D20A, M104T; H16E, N88K; D20A, M104V; D20A, M104L; H16E, M104T; H16E, M104V; N88K, M104V; N88K, E61Q; D20A, E61Q; H16R, D20A; D20W, E61Q; H16E, E61Q; H16E, M104L; N88K, M104T; D20A, H16E; D20A, H16E, E16Q; D20A, H16R, E16Q; V91K, D20W; V91A, H16A; V91A, H16D; V91A, H16E; V91A, H16S; V91E, H16A; V91E, H16D; V91E, H16E; V91E, H16S; V91K, H16A; V91K, H16D; V91K, H16S; and V91S, H16E; and preferentially stimulates T regulatory cells relative to other T cells or NK cells, both in in vitro assays and in humanized mice (NSG mice reconstituted with CD34+ hematopoietic stem cells). In one embodiment, said mutein is at least 95% identical to the amino acid sequence set forth in SEQ ID NO:1. In another embodiment, said mutein is at least 97% identical to the amino acid sequence set forth in SEQ ID NO:1. In another embodiment, the amino acid sequence of said mutein differs from the amino acid sequence set forth in SEQ ID NO:1 only at C125A and at one position selected from V91K, D20L; D84R, E61Q; V91K, D20A, E61Q, M104T; N88K, M104L; V91H, M104L; V91K, H16E, M104V; V91K, H16R, M104V; V91K, H16R, M104T; V91K, D20A, M104T; V91K, H16E, M104T; V91K, H16E, E61Q, M104T; V91K, H16R, E61Q, M104T; V91K, H16E; V91H, D20A, M104T; H16E, V91H; V91H, M104V; V91H, D20A, E61Q, M104T; V91H, H16R, E16Q; V91K, D20A, M104V; H16E, V91H; V91H, D20A, M104V; H16E, V91H, M104T; H16E, V91H, E61Q, M104T; V91K, E61Q, H16E; V91K, H16R, M104L; H16E, V91H, E16Q; V91K, E61Q, H16R; D20W, V91K, E61Q; V91H, H16R; V91K, H16R; D20W, V91K, E61Q, M104T; V91K, D20A; V91H, D20A, E16Q; V91K, D20A, M104L; V91H, D20A; V91K, E61Q, D20A; V91H, M104T; V91H, M104V; V91K, E61Q; V91K, N88K, E61Q, M104T; V91K, N88K, E61Q; V91H, E61Q; V91K, N88K; D20A, H16E, M104T; D20A, M104T; H16E, N88K; D20A, M104V; D20A, M104L; H16E, M104T; H16E, M104V; N88K, M104V; N88K, E61Q; D20A, E61Q; H16R, D20A; D20W, E61Q; H16E, E61Q; H16E, M104L; N88K, M104T; D20A, H16E; D20A, H16E, E16Q; D20A, H16R, E16Q; V91K, D20W; V91A, H16A; V91A, H16D; V91A, H16E; V91A, H16S; V91E, H16A; V91E, H16D; V91E, H16E; V91E, H16S; V91K, H16A; V91K, H16D; V91K, H16S; and V91S, H16E.

In another aspect, the present invention provides an Fc-fusion protein comprising an Fc and the human IL-2 mutein as described above. In one embodiment, the Fc is a human IgG1 Fc. In another embodiment, the human IgG1 Fc comprises one or more mutations altering effector function of said Fc. In another embodiment, the human IgG1 comprises a substitution at N297. In another embodiment, the substitution at N297 is N297G. In another embodiment, the Fc-fusion protein comprises a substitution or deletion of the C-terminal lysine of said human IgG Fc. In another embodiment, the C-terminal lysine of said human IgG Fc is deleted. In another embodiment, a linker connects the Fc and human IL-2 mutein portions of said protein. In another embodiment, the linker is GGGGS (SEQ ID NO: 5), GGNGT, or (SEQ ID NO: 6), and YGNGT (SEQ ID NO: 7). In another embodiment, the linker is GGGGS (SEQ ID NO: 5). In another embodiment, the IL-2 mutein further comprises an amino acid addition, substitution, or deletion altering glycosylation of said Fc-fusion protein when expressed in mammalian cells. In another embodiment, the IL-2 mutein comprises a T3 substitution. In another embodiment, the IL-2 mutein comprises a T3N or T3A substitution. In another embodiment, the IL-2 mutein comprises a T3N substitution. In another embodiment, the IL-2 mutein further comprises an S5 mutation. In another embodiment, the IL-2 mutein further comprises an S5T mutation. In another embodiment, said Fc-fusion protein comprises an Fc dimer. In another embodiment, said Fc-fusion protein comprises two IL-2 muteins. In another embodiment, said Fc-fusion protein comprises a single IL-2 mutein.

In another aspect, the present invention provides an isolated nucleic acid encoding a human IL-2 mutein as described above.

In another aspect, the present invention provides an isolated nucleic acid encoding an Fc portion of an antibody and a human IL-2 mutein as described above. In one embodiment, said Fc portion of an antibody and the human IL-2 mutein are encoded within a single open-reading frame. In another embodiment, the Fc is a human IgG1 Fc. In another embodiment, the human IgG1 Fc comprises one or more mutations altering effector function of said Fc. In another embodiment, the human IgG1 comprises a substitution at N297. In another embodiment, the substitution at N297 is N297G. In another embodiment, the nucleic acid encodes a substitution or deletion of the C-terminal lysine of said human IgG Fc. In another embodiment, the C-terminal lysine of said human IgG Fc is deleted. In another embodiment, the nucleic acid further encodes a linker connecting the Fc portion of an antibody and the human IL-2 mutein. In another embodiment, the linker is GGGGS (SEQ ID NO: 5), GGNGT, or (SEQ ID NO: 6), and YGNGT (SEQ ID NO: 7). In another embodiment, the linker is GGGGS (SEQ ID NO: 5). In another embodiment, the IL-2 mutein further comprises an amino acid addition, substitution, or deletion altering glycosylation of a protein comprising said IL-2 mutein when expressed in mammalian cells. In another embodiment, the IL-2 mutein comprises a T3 substitution. In another embodiment, the IL-2 mutein comprises a T3N or T3A substitution. In another embodiment, the IL-2 mutein comprises a T3N substitution. In another embodiment, the IL-2 mutein further comprises an S5 mutation. In another embodiment, the IL-2 mutein further comprises an S5T mutation.

In another aspect, the present invention provides an expression vector comprising an isolated nucleic acid described above operably linked to a promoter.

In another aspect, the present invention provides a host cell comprising an isolated nucleic acid described above. In one embodiment, the isolated nucleic acid is operably linked to a promoter. In another embodiment, said host cell is a prokaryotic cell. In another embodiment, the host cell is *E. coli*. In another embodiment, said host cell is a eukaryotic cell. In another embodiment, the host cell is a mammalian cell. In another embodiment, the host cell is a Chinese hamster ovary (CHO) cell line.

In another aspect, the present invention provides a method of making a human IL-2 mutein, comprising culturing a host cell as described above under conditions in which said promoter is expressed and harvesting the human IL-2 mutein from said culture.

In another aspect, the present invention provides a method of making a Fc-fusion protein, comprising culturing a host cell as described above under conditions in which said promoter is expressed and harvesting the Fc-fusion protein from said culture.

In another aspect, the present invention provides a method of increasing the ratio of regulatory T cells (Tregs) to non-regulatory T cells within a population of T cells, comprising contacting the population of T cells with an effective amount of a human IL-2 mutein as described above. In one embodiment, the ratio of CD3+FoxP3+ cells to CD3+ FoxP3− increases. In another embodiment, the ratio of CD3+FoxP3+ cells to CD3+FoxP3− increases at least 50%.

In another aspect, the present invention provides a method of increasing the ratio of regulatory T cells (Tregs) to non-regulatory T cells within a population of T cells, comprising contacting the population of T cells with an effective amount of an Fc-fusion protein as described above. In one embodiment, the ratio of CD3+FoxP3+ cells to CD3+ FoxP3− increases. In another embodiment, the ratio of CD3+FoxP3+ cells to CD3+FoxP3− increases at least 50%.

In another aspect, the present invention provides a method of increasing the ratio of regulatory T cells (Tregs) to non-regulatory T cells within peripheral blood of a subject, comprising administering an effective amount of a human IL-2 mutein as described above. In one embodiment, the ratio of CD3+FoxP3+ cells to CD3+FoxP3− increases. In another embodiment, the ratio of CD3+FoxP3+ cells to CD3+FoxP3− increases at least 50%.

In another aspect, the present invention provides a method of increasing the ratio of regulatory T cells (Tregs) to non-regulatory T cells within the peripheral blood of a subject, comprising administering an effective amount of an Fc-fusion protein as described above. In one embodiment, the ratio of CD3+FoxP3+ cells to CD3+FoxP3− increases. In another embodiment, the ratio of CD3+FoxP3+ cells to CD3+FoxP3− increases at least 50%.

In another aspect, the present invention provides a method of increasing the ratio of regulatory T cells (Tregs) to natural killer (NK) cells within the peripheral blood of a subject, comprising administering an effective amount of a human IL-2 mutein as described above. In one embodiment, the ratio of CD3+FoxP3+ cells to CD3–CD19– lymphocytes expressing CD56 and/or CD16 increases. In another embodiment, the ratio of CD3+FoxP3+ cells to CD3–CD19– lymphocytes expressing CD56 and/or CD16 increases at least 50%.

In another aspect, the present invention provides a method of increasing the ratio of regulatory T cells (Tregs) to natural killer (NK) cells within the peripheral blood of a subject, comprising administering an effective amount of an Fc-fusion protein as described above. In one embodiment, the ratio of CD3+FoxP3+ cells to CD3–CD19– lymphocytes expressing CD56 and/or CD16 increases. In another embodiment, the ratio of CD3+FoxP3+ cells to CD3–CD19– lymphocytes expressing CD56 and/or CD16 increases at least 50%.

In another aspect, the present invention provides a method of treating a subject with an inflammatory or autoimmune disease, said method comprising administering to said subject a therapeutically effective amount of an IL-2 mutein as described above or a therapeutically effective amount of an Fc-fusion protein as described above. In one embodiment, administration causes reduction of at least one symptom of the disease. In another embodiment, the ratio of regulatory T cells (Tregs) to non-regulatory T cells within the peripheral blood of a subject increases after the administration. In another embodiment, the ratio of regulatory T cells (Tregs) to non-regulatory T cells within the peripheral blood of a subject remains essentially the same after the administration. In another embodiment, the inflammatory or autoimmune disease is lupus, graft-versus-host disease, hepatitis C-induced vasculitis, type I diabetes, type II diabetes, multiple sclerosis, rheumatoid arthritis, alopecia areata, atherosclerosis, psoriasis, organ transplant rejection, Sjögren's Syndrome, Behcet's disease, spontaneous loss of pregnancy, atopic diseases, asthma, or inflammatory bowel diseases.

DETAILED DESCRIPTION OF PREFERRED EMBODIMENTS

Figure 1:
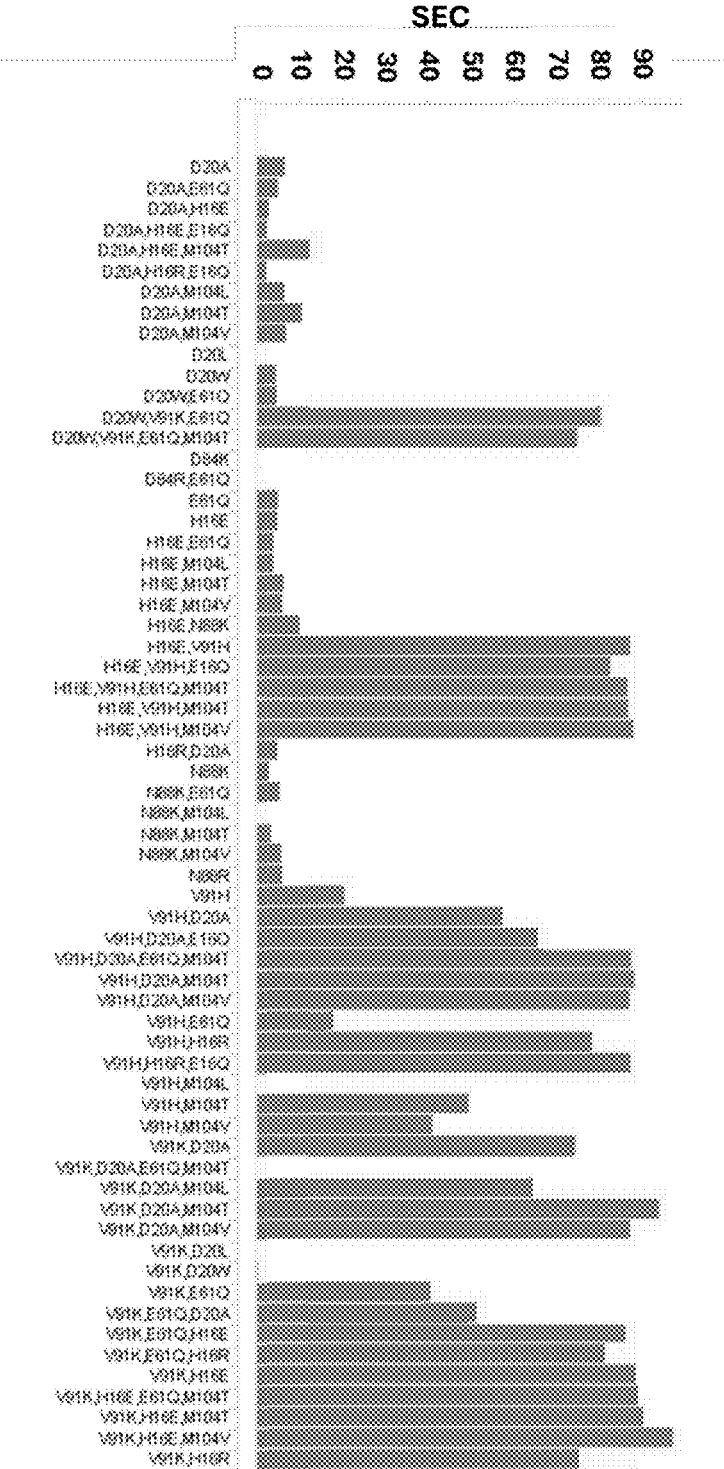
FIG. 1 shows the results of a DSC Tm measurement of IL-2 muteins with 40° C. 10 day stability measured by SEC chromatography.

The section headings used herein are for organizational purposes only and are not to be construed as limiting the subject matter described. All references cited within the body of this specification are expressly incorporated by reference in their entirety.

Standard techniques may be used for recombinant DNA, oligonucleotide synthesis, tissue culture and transformation, protein purification, etc. Enzymatic reactions and purification techniques may be performed according to the manufacturer's specifications or as commonly accomplished in the art or as described herein. The following procedures and techniques may be generally performed according to conventional methods well known in the art and as described in various general and more specific references that are cited and discussed throughout the specification. See, e.g., Sambrook et al., 2001, *Molecular Cloning: A Laboratory Manuel, $3^{rd}$* ed., Cold Spring Harbor Laboratory Press, cold Spring Harbor, N.Y., which is incorporated herein by reference for any purpose. Unless specific definitions are provided, the nomenclature used in connection with, and the laboratory procedures and techniques of, analytic chemistry, organic chemistry, and medicinal and pharmaceutical chemistry described herein are those well known and commonly used in the art. Standard techniques may be used for chemical synthesis, chemical analyses, pharmaceutical preparation, formulation, and delivery and treatment of patients.

IL-2

The IL-2 muteins described herein are variants of wild-type human IL-2. As used herein, "wild-type human IL-2," "wild-type IL-2," or "WT IL-2" shall mean the polypeptide having the following amino acid sequence:

```
                                          (SEQ ID NO: 2)
APTSSSTKKTQLQLEHLLLDLQMILNGINNYKNPKLTRMLTFKFYMPK

KATELKHLQCLEEELKPLEEVLNLAQSKNFHLRPRDLISNINVIVLEL

KGSETTFMCEYADETATIVEFLNRWITFXQSIISTLT
Wherein X is C, S, V, or A.
```

Variants may contain one or more substitutions, deletions, or insertions within the wild-type IL-2 amino acid sequence. Residues are designated herein by the one letter amino acid code followed by the IL-2 amino acid position, e.g., K35 is the lysine residue at position 35 of SEQ ID NO: 2. Substitutions are designated herein by the one letter amino acid code followed by the IL-2 amino acid position followed by the substituting one letter amino acid code, e.g., K35A is a substitution of the lysine residue at position 35 of SEQ ID NO:2 with an alanine residue.

IL-2 Muteins

Provided herein are human IL-2 muteins and anti-IL-2 antibodies that preferentially stimulate T regulatory (Treg) cells. As used herein "preferentially stimulates T regulatory cells" means the mutein or antibody promotes the proliferation, survival, activation and/or function of CD3+FoxP3+ T cells over CD3+FoxP3– T cells. Methods of measuring the ability to preferentially stimulate Tregs can be measured by flow cytometry of peripheral blood leukocytes, in which there is an observed increase in the percentage of FOXP3+ CD4+ T cells among total CD4+ T cells, an increase in percentage of FOXP3+CD8+ T cells among total CD8+ T cells, an increase in percentage of FOXP3+ T cells relative to NK cells, and/or a greater increase in the expression level of CD25 on the surface of FOXP3+ T cells relative to the increase of CD25 expression on other T cells. Preferential growth of Treg cells can also be detected as increased representation of demethylated FOXP3 promoter DNA (i.e. the Treg-specific demethylated region, or TSDR) relative to demethylated CD3 genes in DNA extracted from whole blood, as detected by sequencing of polymerase chain reaction (PCR) products from bisulfite-treated genomic DNA (J. Sehouli, et al. 2011. Epigenetics 6:2, 236-246). In particular, IL-2 muteins of the present invention have an enhanced Treg:Teff window, i.e., those that retained high level of activity in Treg cells while showing significant attenuation in Teff cells. Since activated Teff cells express increased levels of CD25, and patients with autoimmune and inflammatory diseases possess elevated number of these cells, we applied CD25+-gating on Teff cells to mimic the more realistic differentiation in CD25 expression in patients.

IL-2 muteins or Fc-fusion proteins thereof that preferentially stimulate Treg cells increase the ratio of CD3+FoxP3+ T cells over CD3+FoxP3− T cells in a subject or a peripheral blood sample at least 30%, at least 40%, at least 50%, at least 60%, at least 70%, at least 80%, at least 90%, at least 100%, at least 150%, at least 200%, at least 300%, at least 400%, at least 500%, at least 600%, at least 700%, at least 800%, at least 900%, or at least 1000%.

In some embodiments, IL-2 muteins or Fc-fusion proteins thereof, has less than 50% pSTAT activation of T effector cells at 1 nM IL-2 treatment, using the protocol of Example 1. In some embodiments, IL-2 muteins or Fc-fusion proteins thereof, has less than 40% pSTAT activation of T effector cells at 1 nM IL-2 treatment, using the protocol of Example 1. In some embodiments, IL-2 muteins or Fc-fusion proteins thereof, has less than 30% pSTAT activation of T effector cells at 1 nM IL-2 treatment, using the protocol of Example 1. In some embodiments, IL-2 muteins or Fc-fusion proteins thereof, has less than 20% pSTAT activation of T effector cells at 1 nM IL-2 treatment, using the protocol of Example 1. In some embodiments, IL-2 muteins or Fc-fusion proteins thereof, has less than 10% pSTAT activation of T effector cells at 1 nM IL-2 treatment, using the protocol of Example 1. In some embodiments, IL-2 muteins or Fc-fusion proteins thereof, also have a 10-day stability greater than 25%, 30%, 40%, 50%, 60%, 70%, 80%, or 90%, using the protocol of Example 2.

In some embodiments, IL-2 muteins or Fc-fusion proteins thereof, has less than 50% pSTAT activation of T effector cells at 200 nM IL-2 treatment, using the protocol of Example 1. In some embodiments, IL-2 muteins or Fc-fusion proteins thereof, has less than 40% pSTAT activation of T effector cells at 200 nM IL-2 treatment, using the protocol of Example 1. In some embodiments, IL-2 muteins or Fc-fusion proteins thereof, has less than 30% pSTAT activation of T effector cells at 200 nM IL-2 treatment, using the protocol of Example 1. In some embodiments, IL-2 muteins or Fc-fusion proteins thereof, has less than 20% pSTAT activation of T effector cells at 200 nM IL-2 treatment, using the protocol of Example 1. In some embodiments, IL-2 muteins or Fc-fusion proteins thereof, has less than 10% pSTAT activation of T effector cells at 200 nM IL-2 treatment, using the protocol of Example 1. In some embodiments, IL-2 muteins or Fc-fusion proteins thereof, also have a 10-day stability greater than 25%, 30%, 40%, 50%, 60%, 70%, 80%, or 90%, using the protocol of Example 2.

In some embodiments, IL-2 muteins or Fc-fusion proteins thereof, has greater than 30% pSTAT activation of T regulatory cells at 1 nM IL-2 treatment, using the protocol of Example 1. In some embodiments, IL-2 muteins or Fc-fusion proteins thereof, has greater than 40% pSTAT activation of T regulatory cells at 1 nM IL-2 treatment, using the protocol of Example 1. In some embodiments, IL-2 muteins or Fc-fusion proteins thereof, has greater than 50% pSTAT activation of T regulatory cells at 1 nM IL-2 treatment, using the protocol of Example 1. In some embodiments, IL-2 muteins or Fc-fusion proteins thereof, has greater than 60% pSTAT activation of T regulatory cells at 1 nM IL-2 treatment, using the protocol of Example 1. In some embodiments, IL-2 muteins or Fc-fusion proteins thereof, has greater than 70% pSTAT activation of T regulatory cells at 1 nM IL-2 treatment, using the protocol of Example 1. In some embodiments, IL-2 muteins or Fc-fusion proteins thereof, also have a 10-day stability greater than 25%, 30%, 40%, 50%, 60%, 70%, 80%, or 90%, using the protocol of Example 2.

In some embodiments, IL-2 muteins or Fc-fusion proteins thereof, has greater than 30% pSTAT activation of T regulatory cells at 200 nM IL-2 treatment, using the protocol of Example 1. In some embodiments, IL-2 muteins or Fc-fusion proteins thereof, has greater than 40% pSTAT activation of T regulatory cells at 200 nM IL-2 treatment, using the protocol of Example 1. In some embodiments, IL-2 muteins or Fc-fusion proteins thereof, has greater than 50% pSTAT activation of T regulatory cells at 200 nM IL-2 treatment, using the protocol of Example 1. In some embodiments, IL-2 muteins or Fc-fusion proteins thereof, has greater than 60% pSTAT activation of T regulatory cells at 200 nM IL-2 treatment, using the protocol of Example 1. In some embodiments, IL-2 muteins or Fc-fusion proteins thereof, has greater than 70% pSTAT activation of T regulatory cells at 200 nM IL-2 treatment, using the protocol of Example 1. In some embodiments, IL-2 muteins or Fc-fusion proteins thereof, also have a 10-day stability greater than 25%, 30%, 40%, 50%, 60%, 70%, 80%, or 90%, using the protocol of Example 2.

Examples of IL-2 muteins include, but are not limited to, IL-2 muteins comprising V91K, D20L; D84R, E61Q; V91K, D20A, E61Q, M104T; N88K, M104L; V91H, M104L; V91K, H16E, M104V; V91K, H16R, M104V; V91K, H16R, M104T; V91K, D20A, M104T; V91K, H16E, M104T; V91K, H16E, E61Q, M104T; V91K, H16R, E61Q, M104T; V91K, H16E; V91H, D20A, M104T; H16E, V91H, M104V; V91H, D20A, E61Q, M104T; V91H, H16R, E16Q; V91K, D20A, M104V; H16E, V91H; V91H, D20A, M104V; H16E, V91H, M104T; H16E, V91H, E61Q, M104T; V91K, E61Q, H16E; V91K, H16R, M104L; H16E, V91H, E16Q; V91K, E61Q, H16R; D20W, V91K, E61Q; V91H, H16R; V91K, H16R; D20W, V91K, E61Q, M104T; V91K, D20A; V91H, D20A, E16Q; V91K, D20A, M104L; V91H, D20A; V91K, E61Q, D20A; V91H, M104T; V91H, M104V; V91K, E61Q; V91K, N88K, E61Q, M104T; V91K, N88K, E61Q; V91H, E61Q; V91K, N88K; D20A, H16E, M104T; D20A, M104T; H16E, N88K; D20A, M104V; D20A, M104L; H16E, M104T; H16E, M104V; N88K, M104V; N88K, E61Q; D20A, E61Q; H16R, D20A; D20W, E61Q; H16E, E61Q; H16E, M104L; N88K, M104T; D20A, H16E; D20A, H16E, E16Q; D20A, H16R, E16Q; V91K, D20W; V91A, H16A; V91A, H16D; V91A, H16E; V91A, H16S; V91E, H16A; V91E, H16D; V91E, H16E; V91E, H16S; V91K, H16A; V91K, H16D; V91K, H16S; and/or V91S, H16E substitution(s) in the amino acid sequence set forth in SEQ ID NO:2. IL-2 muteins of the present invention optionally comprise a C125A substitution. Although it may be advantageous to reduce the number of further mutations to the wild-type IL-2 sequence, the invention includes IL-2 muteins also including truncations and/or additional insertions, deletions, and/or substitutions in addition to the V91K, D20L; D84R, E61Q; V91K, D20A, E61Q, M104T; N88K, M104L; V91H, M104L; V91K, H16E, M104V; V91K, H16R, M104V; V91K, H16R, M104T; V91K, D20A, M104T; V91K, H16E, M104T; V91K, H16E, E61Q, M104T; V91K, H16R, E61Q, M104T; V91K, H16E; V91H, D20A, M104T; H16E, V91H, M104V; V91H, D20A, E61Q, M104T; H16E, V91H; V91H, D20A, M104V; H16E, V91H, M104T; H16E, V91H; V91H, E61Q, M104T; V91K, E61Q, H16E; V91K, H16R, M104L; H16E, V91H, E16Q; V91K, E61Q, H16R; D20W, V91K, E61Q; V91H, H16R; V91K, H16R; D20W, V91K, E61Q, M104T; V91K, D20A; V91H, D20A, E16Q; V91K, D20A, M104L; V91H, D20A; V91K, E61Q, D20A; V91H, M104T; V91H, M104V; V91K, E61Q; V91K, N88K, E61Q, M104T; V91K, N88K, E61Q; V91H, E61Q; V91K, N88K; D20A, H16E, M104T; D20A, M104T; H16E, N88K; D20A, M104V; D20A, M104L; H16E, M104T; H16E, M104V; N88K, M104V; N88K, E61Q; D20A, E61Q; H16R, D20A; D20W, E61Q; H16E, E61Q; H16E, M104L; N88K, M104T; D20A, H16E; D20A, H16E, E16Q; D20A, H16R, E16Q; V91K, D20W; V91A, H16A; V91A, H16D; V91A, H16E; V91A, H16S; V91E, H16A; V91E, H16D; V91E, H16E; V91E, H16S; V91K, H16A; V91K, H16D; V91K, H16S; and/or V91S, H16E substitution, provided that said muteins maintain the activity of preferentially simulating Tregs. Thus, embodiments include IL-2 muteins that preferentially stimulate Treg cells and comprise an amino acid sequence having a V91K, D20L; D84R, E61Q; V91K, D20A, E61Q, M104T; N88K, M104L; V91H, M104L; V91K, H16E, M104V; V91K, H16R, M104V; V91K, H16R, M104T; V91K, D20A, M104T; V91K, H16E, M104T; V91K, H16E, E61Q, M104T; V91K, H16R, E61Q, M104T; V91K, H16E; V91H, D20A, M104T; H16E, V91H, M104V; V91H, D20A, E61Q, M104T; V91H, H16R, E16Q; V91K, D20A, M104V; H16E, V91H; V91H, D20A, M104V; H16E, V91H, M104T; H16E, V91H, E61Q, M104T; V91K, E61Q, H16E; V91K, H16R, M104L; H16E, V91H, E16Q; V91K, E61Q, H16R; D20W, V91K, E61Q; V91H, H16R; V91K, H16R; D20W, V91K, E61Q, M104T; V91K, D20A; V91H, D20A, E16Q; V91K, D20A, M104L; V91H, D20A; V91K, E61Q, D20A; V91H, M104T; V91H, M104V; V91K, E61Q; V91K, N88K, E61Q, M104T; V91K, N88K, E61Q; V91H, E61Q; V91K, N88K; D20A, H16E, M104T; D20A, M104T; H16E, N88K; D20A, M104V; D20A, M104L; H16E, M104T; H16E, M104V; N88K, M104V; N88K, E61Q; D20A, E61Q; H16R, D20A; D20W, E61Q; H16E, E61Q; H16E, M104L; N88K, M104T; D20A, H16E; D20A, H16E, E16Q; D20A, H16R, E16Q; V91K, D20W; V91A, H16A; V91A, H16D; V91A, H16E; V91A, H16S; V91E, H16A; V91E, H16D; V91E, H16E; V91E, H16S; V91K, H16A; V91K, H16D; V91K, H16S; and/or V91S, H16E substitution and that is at least 90%, at least 91%, at least 92%, at least 93%, at least 94%, at least 95%, at least 96%, at least 97%, at least 98%, or at least 99% identical to the amino acid sequence set forth in SEQ ID NO:2. In particularly preferred embodiments, such IL-2 muteins comprise an amino acid sequence that is at least 90%, at least 91%, at least 92%, at least 93%, at least 94%, at least 95%, at least 96%, at least 97%, at least 98%, or at least 99% identical to the amino acid sequence set forth in SEQ ID NO:2.

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

While the site or region for introducing an amino acid sequence variation may be predetermined, the mutation per se need not be predetermined. For example, in order to optimize the performance of a mutation at a given site, random mutagenesis may be conducted at the target codon or region and the expressed IL-2 mutein screened for the optimal combination of desired activity. Techniques for making substitution mutations at predetermined sites in DNA having a known sequence are well known, for example, M13 primer mutagenesis and PCR mutagenesis. Screening of the mutants may be done using assays described herein, for example.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances. Conservative substitutions are generally made in accordance with the following chart depicted as TABLE 1.

TABLE 1

| Original Residue | Exemplary Substitutions |
| --- | --- |
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr, Trp |
| Ser | Thr |
| Thr | Ser |
| Trp | Tyr, Phe |
| Tyr | Trp, Phe |
| Val | Ile, Leu |

Substantial changes in function or immunological identity are made by selecting substitutions that are less conservative than those shown in TABLE 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the IL-2 mutein as needed. Alternatively, the variant may be designed such that the biological activity of the IL-2 mutein is altered. For example, glycosylation sites may be altered or removed as discussed herein.

IL-2 Muteins Having Extended Serum Half-Life

Because the IL-2 muteins provided herein preferentially expand Tregs over, for example Teff or NK cells, it is expected that the safety profile when administered to a patient will differ from that of wild-type IL-2 or PRO-LEUKIN® (aldesleukin; Novartis, Basel, Switzerland). Side-effects associated with wild-type IL-2 or PRO-LEUKIN® include flu-like symptoms, chills/rigor, arthralgia, fever, rash, pruritus, injection site reactions, hypotension, diarrhea, nausea, anxiety, confusion, and depression. The IL-2 muteins provided herein may be altered to include or fused to molecules that extend the serum half-life of the mutein without increasing the risk that such half-life extension would increase the likelihood or the intensity of a side-effect or adverse event in a patient. Subcutaneous dosing of such an extended serum half-life mutein may allow for prolonged target coverage with lower systemic maximal exposure ($C_{max}$). Extended serum half-life may allow a lower or less frequent dosing regimen of the mutein.

The serum half-life of the IL-2 muteins provided herein may be extended by essentially any method known in the art. Such methods include altering the sequence of the IL-2 mutein to include a peptide that binds to the neonatal Fcγ receptor or bind to a protein having extended serum half-life, e.g., IgG or human serum albumin. In other embodiments, the IL-2 mutein is fused to a polypeptide that confers extended half-life on the fusion molecule. Such polypeptides include an IgG Fc or other polypeptides that bind to the neonatal Fcγ receptor, human serum albumin, or polypeptides that bind to a protein having extended serum half-life. In preferred embodiments, the IL-2 mutein is fused to an IgG Fc molecule.

The IL-2 mutein may be fused to the N-terminus or the C-terminus of the IgG Fc region. As shown in the Examples, fusion to the C-terminus of the IgG Fc region maintains the IL-2 mutein activity to a greater extent than when fused to the N-terminus of the IgG Fc.

One embodiment of the present invention is directed to a dimer comprising two Fc-fusion polypeptides created by fusing an IL-2 mutein to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain bonds form between the Fc moieties to yield the dimer.

The term "Fc polypeptide" or "Fc region" as used herein includes native and mutein forms of polypeptides derived from the Fc region of an antibody and can be part of either the IL-2 mutein fusion proteins or the anti-IL-2 antibodies of the invention. Truncated forms of such polypeptides containing the hinge region that promotes dimerization also are included. In certain embodiments, the Fc region comprises an antibody CH2 and CH3 domain. Along with extended serum half-life, fusion proteins comprising Fc moieties (and oligomers formed therefrom) offer the advantage of facile purification by affinity chromatography over Protein A or Protein G columns. Preferred Fc regions are derived from human IgG, which includes IgG1, IgG2, IgG3, and IgG4. Herein, specific residues within the Fc are identified by position. All Fc positions are based on the EU numbering scheme.

One of the functions of the Fc portion of an antibody is to communicate to the immune system when the antibody binds its target. This is considered "effector function." Communication leads to antibody-dependent cellular cytotoxicity (ADCC), antibody-dependent cellular phagocytosis (ADCP), and/or complement dependent cytotoxicity (CDC). ADCC and ADCP are mediated through the binding of the Fc to Fc receptors on the surface of cells of the immune system. CDC is mediated through the binding of the Fc with proteins of the complement system, e.g., C1q.

The IgG subclasses vary in their ability to mediate effector functions. For example, IgG1 is much superior to IgG2 and IgG4 at mediating ADCC and CDC. Thus, in embodiments wherein effector function is undesirable, an IgG2 Fc would be preferred. IgG2 Fc-containing molecules, however, are known to be more difficult to manufacture and have less attractive biophysical properties, such as a shorter half-life, as compared to IgG1 Fc-containing molecules.

The effector function of an antibody can be increased, or decreased, by introducing one or more mutations into the Fc. Embodiments of the invention include IL-2 mutein Fc fusion proteins having an Fc engineered to increase effector function (U.S. Pat. No. 7,317,091 and Strohl, *Curr. Opin. Bio-*

*tech.*, 20:685-691, 2009; both incorporated herein by reference in its entirety). Exemplary IgG1 Fc molecules having increased effector function include those having the following substitutions: S239D/I332E; S239D/A330S/I332E; S239D/A330L/I332E; S298A/D333A/K334A; P247I/A339D; P247I/A339Q; D280H/K290S; D280H/K290S/S298D; D280H/K290S/S298V; F243L/R292P/Y300L; F243L/R292P/Y300L/P396L; F243L/R292P/Y300L/V305I/P396L; G236A/S239D/I332E; K326A/E333A; K326W/E333S; K290E/S298G/T299A; K290N/S298G/T299A; K290E/S298G/T299A/K326E; and/or K290N/S298G/T299A/K326E.

Another method of increasing effector function of IgG Fc-containing proteins is by reducing the fucosylation of the Fc. Removal of the core fucose from the biantennary complex-type oligosaccharides attached to the Fc greatly increased ADCC effector function without altering antigen binding or CDC effector function. Several ways are known for reducing or abolishing fucosylation of Fc-containing molecules, e.g., antibodies. These include recombinant expression in certain mammalian cell lines including a FUT8 knockout cell line, variant CHO line Lec13, rat hybridoma cell line YB2/0, a cell line comprising a small interfering RNA specifically against the FUT8 gene, and a cell line coexpressing β-1,4-N-acetylglucosaminyltransferase III and Golgi α-mannosidase II. Alternatively, the Fc-containing molecule may be expressed in a non-mammalian cell such as a plant cell, yeast, or prokaryotic cell, e.g., *E. coli*.

In certain embodiments, the IL-2 mutein Fc-fusion proteins or anti-IL-2 antibodies of the invention comprise an Fc engineered to decrease effector function. Exemplary Fc molecules having decreased effector function include those having the following substitutions: N297A or N297Q (IgG1); L234A/L235A (IgG1); V234A/G237A (IgG2); L235A/G237A/E318A (IgG4); H268Q/V309L/A330S/A331S (IgG2); C220S/C226S/C229S/P238S (IgG1); C226S/C229S/E233P/L234V/L235A (IgG1); L234F/L235E/P331S (IgG1); and/or S267E/L328F (IgG1).

It is known that human IgG1 has a glycosylation site at N297 (EU numbering system) and glycosylation contributes to the effector function of IgG1 antibodies. An exemplary IgG1 sequence is provided in SEQ ID NO:3:

```
Asp Lys Thr His Thr Cys Pro Pro Cys Pro Ala Pro
1               5                   10

Glu Leu Leu Gly Gly Pro Ser Val Phe Leu Phe Pro
            15                  20

Pro Lys Pro Lys Asp Thr Leu Met Ile Ser Arg Thr
25                  30                  35

Pro Glu Val Thr Cys Val Val Val Asp Val Ser His
            40                  45

Glu Asp Pro Glu Val Lys Phe Asn Trp Tyr Val Asp
    50                  55                  60

Gly Val Glu Val His Asn Ala Lys Thr Lys Pro Arg
            65                  70

Glu Glu Gln Tyr Asn Ser Thr Tyr Arg Val Val Ser
    75                  80

Val Leu Thr Val Leu His Gln Asp Trp Leu Asn Gly
85                  90                  95

Lys Glu Tyr Lys Cys Lys Val Ser Asn Lys Ala Leu
            100                 105
```

-continued

```
Pro Ala Pro Ile Glu Lys Thr Ile Ser Lys Ala Lys
    110                 115                 120

Gly Gln Pro Arg Glu Pro Gln Val Tyr Thr Leu Pro
            125                 130

Pro Ser Arg Glu Glu Met Thr Lys Asn Gln Val Ser
        135                 140

Leu Thr Cys Leu Val Lys Gly Phe Tyr Pro Ser Asp
145                 150                 155

Ile Ala Val Glu Trp Glu Ser Asn Gly Gln Pro Glu
            160                 165

Asn Asn Tyr Lys Thr Thr Pro Pro Val Leu Asp Ser
    170                 175                 180

Asp Gly Ser Phe Phe Leu Tyr Ser Lys Leu Thr Val
            185                 190

Asp Lys Ser Arg Trp Gln Gln Gly Asn Val Phe Ser
        195                 200

Cys Ser Val Met His Glu Ala Leu His Asn His Tyr
205                 210                 215

Thr Gln Lys Ser Leu Ser Leu Ser Pro Gly Lys
            220                 225
```

Groups have mutated N297 in an effort to make aglycosylated antibodies. The mutations have focuses on substituting N297 with amino acids that resemble asparagine in physiochemical nature such as glutamine (N297Q) or with alanine (N297A) which mimics asparagines without polar groups.

As used herein, "aglycosylated antibody" or "aglycosylated fc" refers to the glycosylation status of the residue at position 297 of the Fc. An antibody or other molecule may contain glycosylation at one or more other locations but may still be considered an aglycosylated antibody or aglycosylated Fc-fusion protein.

In the effort to make an effector functionless IgG1 Fc, it was discovered that mutation of amino acid N297 of human IgG1 to glycine, i.e., N297G, provides far superior purification efficiency and biophysical properties over other amino acid substitutions at that residue. See Example 8. Thus, in preferred embodiments, the IL-2 mutein Fc-fusion protein comprises a human IgG1 Fc having a N297G substitution. The Fc comprising the N297G substitution is useful in any context wherein a molecule comprises a human IgG1 Fc, and is not limited to use in the context of an IL-2 mutein Fc-fusion. In certain embodiments, an antibody comprises the Fc having a N297G substitution.

An Fc comprising a human IgG1 Fc having the N297G mutation may also comprise further insertions, deletions, and substitutions. In certain embodiments the human IgG1 Fc comprises the N297G substitution and is at least 90% identical, at least 91% identical, at least 92% identical, at least 93% identical, at least 94% identical, at least 95% identical, at least 96% identical, at least 97% identical, at least 98% identical, or at least 99% identical to the amino acid sequence set forth in SEQ ID NO:3. In a particularly preferred embodiment, the C-terminal lysine residue is substituted or deleted. The amino acid sequence of human IgG1 comprising the N297G substitution and deletion of the C-terminal lysine is set forth in SEQ ID NO:4.

A glycosylated IgG1 Fc-containing molecules were shown to be less stable than glycosylated IgG1 Fc-containing molecules. The Fc region may be further engineered to increase the stability of the aglycosylated molecule. In some embodiments, one or more amino acids are substituted to cysteine so to form di-sulfide bonds in the dimeric state. Residues V259, A287, R292, V302, L306, V323, or I332 of the amino acid sequence set forth in SEQ ID NO:3 may be substituted with cysteine. In preferred embodiments, specific pairs of residues are substitution such that they preferentially form a di-sulfide bond with each other, thus limiting or preventing di-sulfide bond scrambling. Preferred pairs include, but are not limited to, A287C and L306C, V259C and L306C, R292C and V302C, and V323C and I332C.

Provided herein are Fc-containing molecules wherein one or more of residues V259, A287, R292, V302, L306, V323, or I332 are substituted with cysteine, examples of which include those comprising A287C and L306C, V259C and L306C, R292C and V302C, or V323C and I332C substitutions.

Additional mutations that may be made to the IgG1 Fc include those facilitate heterodimer formation amongst Fc-containing polypeptides. In some embodiments, Fc region is engineering to create "knobs" and "holes" which facilitate heterodimer formation of two different Fc-containing polypeptide chains when co-expressed in a cell. U.S. Pat. No. 7,695,963. In other embodiments, the Fc region is altered to use electrostatic steering to encourage heterodimer formation while discouraging homodimer formation of two different Fc-containing polypeptide when co-expressed in a cell. WO 09/089,004, which is incorporated herein by reference in its entirety. Preferred heterodimeric Fc include those wherein one chain of the Fc comprises D399K and E356K substitutions and the other chain of the Fc comprises K409D and K392D substitutions. In other embodiments, one chain of the Fc comprises D399K, E356K, and E357K substitutions and the other chain of the Fc comprises K409D, K392D, and K370D substitutions.

In certain embodiments, it may be advantageous for the IL-2 mutein Fc-fusion protein to be monomeric, i.e., contain only a single IL-2 mutein molecule. Similarly, a bi-, tri-, or tetra-specific antibody that can specifically bind one or more additional targets may be desired. In such embodiments, the Fc-region of the fusion protein or antibody may contain one or more mutations that facilitate heterodimer formation. The fusion protein or antibody is co-expressed with an Fc-region having reciprocal mutations to those in the IL-2 mutein Fc-fusion polypeptide but lacking an IL-2 mutein or anti-IL-2 heavy chain variable domain. When the heterodimer of the two Fc-containing polypeptides forms, the resulting protein comprises only a single IL-2 mutein or anti-IL-2 binding domain.

Another method of creating a monomeric IL-2 mutein Fc-fusion protein is fusing the IL-2 mutein to a monomeric Fc, i.e., an Fc region that does not dimerize. Stable monomeric Fcs comprise mutations that discourage dimerization and that stabilize the molecule in the monomeric form. Preferred monomeric Fcs are disclosed in WO 2011/063348, which is incorporated herein by reference in its entirety. In certain embodiments, IL-2 mutein Fc fusion proteins comprise an Fc comprising negatively charged amino acids at positions 392 and 409 along with a threonine substitution at Y349, L351, L368, V397, L398, F405, or Y407.

In certain embodiments, the IL-2 mutein Fc-fusion protein comprises a linker between the Fc and the IL-2 mutein. Many different linker polypeptides are known in the art and may be used in the context of an IL-2 mutein Fc-fusion protein. In preferred embodiments, the IL-2 mutein Fc-fusion protein comprises one or more copies of a peptide consisting of GGGGS (SEQ ID NO:5), GGNGT (SEQ ID NO: 6), or YGNGT (SEQ ID NO: 7) between the Fc and the IL-2 mutein. In some embodiments, the polypeptide region between the Fc region and the IL-2 mutein region comprises a single copy of GGGGS (SEQ ID NO: 5), GGNGT (SEQ ID NO: 6), or YGNGT (SEQ ID NO: 7). As shown herein, the linkers GGNGT (SEQ ID NO: 6) or YGNGT (SEQ ID NO: 7) are glycosylated when expressed in the appropriate cells and such glycosylation may help stabilize the protein in solution and/or when administered in vivo. Thus, in certain embodiments, an IL-2 mutein fusion protein comprises a glycosylated linker between the Fc region and the IL-2 mutein region.

It is contemplated that the glycosylated linker may be useful when placed in the context of a polypeptide. Provided herein are polypeptides comprising GGNGT (SEQ ID NO: 6) or YGNGT (SEQ ID NO: 7) inserted into the amino acid sequence of the polypeptide or replacing one or more amino acids within the amino acid sequence of the polypeptide. In preferred embodiments, GGNGT (SEQ ID NO: 6) or YGNGT (SEQ ID NO: 7) is inserted into a loop of the polypeptides tertiary structure. In other embodiments, one or more amino acids of a loop are replaced with GGNGT (SEQ ID NO: 6) or YGNGT (SEQ ID NO: 7).

The C-terminal portion of the Fc and/or the amino terminal portion of the IL-2 mutein may contain one or more mutations that alter the glycosylation profile of the IL-2 mutein Fc-fusion protein when expressed in mammalian cells. In certain embodiments, the IL-2 mutein further comprises a T3 substitution, e.g., T3N or T3A. The IL-2 mutein may further comprise an S5 substitution, such as S5T Covalent modifications of IL-2 mutein and IL-2 mutein Fc-fusion proteins and anti-IL-2 antibodies are included within the scope of this invention, and are generally, but not always, done post-translationally. For example, several types of covalent modifications are introduced into the molecule by reacting certain of its amino acid residues with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidazoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidazole and tetranitromethane are used to form 0-acetyl tyrosyl species and 3-nitro derivatives, respectively. Tyrosyl residues are iodinated using $^{125}$I or $^{131}$I to prepare labeled proteins for use in radioimmunoassay, the chloramine T method described above being suitable.

Carboxyl side groups (aspartyl or glutamyl) are selectively modified by reaction with carbodiimides (R'—N═C═N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antigen binding proteins to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Another type of covalent modification of the IL-2 mutein, IL-2 mutein Fc-fusion, or anti-IL-2 antibody included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the IL-2 mutein, IL-2 mutein Fc-fusion, or anti-IL-2 antibody may be conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the IL-2 mutein, IL-2 mutein Fc-fusion, or anti-IL-2 antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the IL-2 mutein, IL-2 mutein Fc-fusion, or anti-IL-2 antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, CRC Crit. Rev. Biochem., pp. 259-306.

Removal of carbohydrate moieties present on the starting IL-2 mutein, IL-2 mutein Fc-fusion, or anti-IL-2 antibody may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131. Enzymatic cleavage of carbohydrate moieties on polypeptides can be achieved by the use of a variety of endo- and exo-glycosidases as described by Thotakura et al., 1987, Meth. Enzymol. 138:350. Glycosylation at potential glycosylation sites may be prevented by the use of the compound tunicamycin as described by Duskin et al., 1982, J. Biol. Chem. 257:3105. Tunicamycin blocks the formation of protein-N-glycoside linkages.

Another type of covalent modification of the IL-2 mutein, IL-2 mutein Fc-fusion, or anti-IL-2 antibody comprises linking the protein to various nonproteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In addition, amino acid substitutions may be made in various positions within the IL-2 mutein, IL-2 mutein Fc-fusion, or anti-IL-2 antibody to facilitate the addition of polymers such as PEG. Thus, embodiments of the invention include PEGylated IL-2 mutein, IL-2 mutein Fc-fusion, or anti-IL-2 antibody. Such PEGylated proteins may have increased half-life and/or reduced immunogenicity over their non-PEGylated forms.

Polynucleotides Encoding IL-2 Muteins and IL-2 Mutein Fc-Fusion Proteins

Encompassed within the invention are nucleic acids encoding IL-2 muteins, IL-2 mutein Fc-fusions, or anti-IL-2 antibodies. Aspects of the invention include polynucleotide variants (e.g., due to degeneracy) that encode the amino acid sequences described herein.

Nucleotide sequences corresponding to the amino acid sequences described herein, to be used as probes or primers for the isolation of nucleic acids or as query sequences for database searches, can be obtained by "back-translation" from the amino acid sequences. The well-known polymerase chain reaction (PCR) procedure can be employed to isolate and amplify a DNA sequence encoding IL-2 muteins and IL-2 mutein Fc-fusion protein. Oligonucleotides that define the desired termini of the combination of DNA fragments are employed as 5' and 3' primers. The oligonucleotides can additionally contain recognition sites for restriction endonucleases, to facilitate insertion of the amplified combination of DNA fragments into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et. al., eds., Academic Press, Inc. (1990).

Nucleic acid molecules of the invention include DNA and RNA in both single-stranded and double-stranded form, as well as the corresponding complementary sequences. An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual,* 2nd ed., Cold Spring Harbor Laboratory, Cold Spring Harbor, NY (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The IL-2 muteins according to the invention are ordinarily prepared by site specific mutagenesis of nucleotides in the DNA encoding the IL-2 mutein or IL-2 mutein Fc-fusion protein, using cassette or PCR mutagenesis or other techniques well known in the art, to produce DNA encoding the variant, and thereafter expressing the recombinant DNA in cell culture as outlined herein. However, IL-2 muteins and IL-2 mutein Fc-fusion may be prepared by in vitro synthesis using established techniques. The variants typically exhibit the same qualitative biological activity as the naturally occurring analogue, e.g., Treg expansion, although variants can also be selected which have modified characteristics as will be more fully outlined below.

As will be appreciated by those in the art, due to the degeneracy of the genetic code, each IL-2 mutein, IL-2 mutein Fc-fusion, and anti-IL-2 antibody of the present invention is encoded by an extremely large number of nucleic acids, each of which is within the scope of the invention and can be made using standard techniques. Thus, having identified a particular amino acid sequence, those skilled in the art could make any number of different nucleic acids, by simply modifying the sequence of one or more codons in a way that does not change the amino acid sequence of the encoded protein.

The present invention also provides expression systems and constructs in the form of plasmids, expression vectors, transcription or expression cassettes which comprise at least one polynucleotide as above. In addition, the invention provides host cells comprising such expression systems or constructs.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the IL-2 mutein, IL-2 mutein Fc-fusion, or anti-IL-2 antibody-encoding sequence; the oligonucleotide sequence encodes polyHis (such as hexaHis (SEQ ID NO: 8)), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of it from the host cell. Affinity purification can be accomplished, for example, by column chromatography using antibodies against the tag as an affinity matrix. Optionally, the tag can subsequently be removed by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, CA), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, MA) is suitable for most gram-negative bacteria, and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and, consequently, of a gene that encodes a desired polypeptide, such as an IL-2 mutein, IL-2 mutein Fc-fusion, or the heavy and/or light chain of an anti-IL-2 antibody. As a result, increased quantities of the polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the IL-2 mutein, IL-2 mutein Fc-fusion, or the heavy and/or light chain of an anti-IL-2 antibody. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thornsen et al., 1984, *Proc. Natl. Acad. U.S.A.* 81:659-663); the promoter contained in the 3' long terminal repeat of Rous sarcoma virus (Yamamoto et al., 1980, *Cell* 22:787-

797); herpes thymidine kinase promoter (Wagner et al., 1981, *Proc. Natl. Acad. Sci. U.S.A.* 78:1444-1445); promoter and regulatory sequences from the metallothionine gene Prinster et al., 1982, *Nature* 296:39-42); and prokaryotic promoters such as the beta-lactamase promoter (Villa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315:115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feto-protein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence may be inserted into the vector to increase transcription by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the IL-2 mutein, IL-2 mutein Fc-fusion, or heavy and/or light chain of an anti-IL-2 antibody. The choice of signal peptide or leader depends on the type of host cells in which the protein is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846. In one embodiment, IL-2 mutein Fc-fusions of the invention comprise a leader sequence as illustrated in FIG. 24.

The vector may contain one or more elements that facilitate expression when the vector is integrated into the host cell genome. Examples include an EASE element (Aldrich et al. 2003 *Biotechnol Prog.* 19:1433-38) and a matrix attachment region (MAR). MARs mediate structural organization of the chromatin and may insulate the integrated vector from "position" effect. Thus, MARs are particularly useful when the vector is used to create stable transfectants. A number of natural and synthetic MAR-containing nucleic acids are known in the art, e.g., U.S. Pat. Nos. 6,239,328; 7,326,567; 6,177,612; 6,388,066; 6,245,974; 7,259,010; 6,037,525; 7,422,874; 7,129,062.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding an IL-2 mutein, IL-2 mutein Fc-fusion, or the heavy and/or light chain of anti-IL-2 antibody has been inserted into the proper site of the vector, the completed vector may be inserted into a suitable host cell for amplification and/or polypeptide expression. The transformation of an expression vector into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an IL-2 mutein, IL-2 mutein Fc-fusion, or the heavy and/or light chain of an anti-IL-2 antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell may be eukaryotic or prokaryotic.

Mammalian cell lines available as hosts for expression are well known in the art and include, but are not limited to, immortalized cell lines available from the American Type Culture Collection (ATCC) and any cell lines used in an expression system known in the art can be used to make the recombinant polypeptides of the invention. In general, host cells are transformed with a recombinant expression vector that comprises DNA encoding a desired IL-2 mutein, IL-2 mutein Fc-fusion, or anti-IL-2 antibody. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, or their derivatives such as Veggie CHO and related cell lines which grow in serum-free media (Rasmussen et al., 1998, *Cytotechnology* 28: 31), HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821, human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Optionally, mammalian cell lines such as HepG2/3B, KB, NIH 3T3 or S49, for example, can be used for expression of the polypeptide when it is desirable to use the polypeptide in various signal transduction or reporter assays.

Alternatively, it is possible to produce the polypeptide in lower eukaryotes such as yeast or in prokaryotes such as bacteria. Suitable yeasts include *Saccharomyces cerevisiae, Schizosaccharomyces pombe, Kluyveromyces strains, Candida*, or any yeast strain capable of expressing heterologous polypeptides. Suitable bacterial strains include *Escherichia coli, Bacillus subtilis, Salmonella typhimurium*, or any bacterial strain capable of expressing heterologous polypeptides. If the polypeptide is made in yeast or bacteria, it may be desirable to modify the polypeptide produced therein, for example by phosphorylation or glycosylation of the appropriate sites, in order to obtain the functional polypeptide. Such covalent attachments can be accomplished using known chemical or enzymatic methods.

The polypeptide can also be produced by operably linking the isolated nucleic acid of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, Texas Agricultural Experiment Station Bulletin No. 1555 (1987), and Luckow and Summers, *Bio/Technology* 6:47 (1988). Cell-free translation systems could also be employed to produce polypeptides using RNAs derived from nucleic acid constructs disclosed herein. Appropriate cloning and expression vectors for use with bacterial, fungal, yeast, and mammalian cellular hosts are described by Pouwels et al. (*Cloning Vectors: A Laboratory Manual, Elsevier*, New York, 1985). A host cell that comprises an isolated nucleic acid of the invention, preferably operably linked to at least one expression control sequence, is a "recombinant host cell".

In certain aspects, the invention includes an isolated nucleic acid encoding a human IL-2 mutein that preferentially stimulates T regulatory cells and comprises a V91K, D20L; D84R, E61Q; V91K, D20A, E61Q, M104T; N88K, M104L; V91H, M104L; V91K, H16E, M104V; V91K, H16R, M104V; V91K, H16R, M104T; V91K, D20A, M104T; V91K, H16E, M104T; V91K, H16E, E61Q, M104T; V91K, H16R, E61Q, M104T; V91K, H16E; V91H, D20A, M104T; H16E, V91H, M104V; V91H, D20A, E61Q, M104T; V91H, H16R, E16Q; V91K, D20A, M104V; H16E, V91H; V91H, D20A, M104V; H16E, V91H, M104T; H16E, V91H, E61Q, M104T; V91K, E61Q, H16E; V91K, H16R, M104L; H16E, V91H, E16Q; V91K, E61Q, H16R; D20W, V91K, E61Q; V91H, H16R; V91K, H16R; D20W, V91K, E61Q, M104T; V91K, D20A; V91H, D20A, E16Q; V91K, D20A, M104L; V91H, D20A; V91K, E61Q, D20A; V91H, M104T; V91H, M104V; V91K, E61Q; V91K, N88K, E61Q, M104T; V91K, N88K, E61Q; V91H, E61Q; V91K, N88K; D20A, H16E, M104T; D20A, M104T; H16E, N88K; D20A, M104V; D20A, M104L; H16E, M104T; H16E, M104V; N88K, M104V; N88K, E61Q; D20A, E61Q; H16R, D20A; D20W, E61Q; H16E, E61Q; H16E, M104L; N88K, M104T; D20A, H16E; D20A, H16E, E16Q; D20A, H16R, E16Q; V91K, D20W; V91A, H16A; V91A, H16D; V91A, H16E; V91A, H16S; V91E, H16A; V91E, H16D; V91E, H16E; V91E, H16S; V91K, H16A; V91K, H16D; V91K, H16S; and/or V91S, H16E substitution and an amino acid sequence at least 90%, at least 91%, at least 92%, at least 93%, at least 94%, at least 95%, at least 96%, at least 97%, at least 98%, at least 99%, or 100% identical to the amino acid sequence set forth in SEQ ID NO:1.

Also included are isolated nucleic acids encoding any of the exemplary IL-2 mutein Fc-fusion proteins described herein. In preferred embodiments, the Fc portion of an antibody and the human IL-2 mutein are encoded within a single open-reading frame, optionally with a linker encoded between the Fc region and the IL-2 mutein.

In another aspect, provided herein are expression vectors comprising the above IL-2 mutein- or IL-2 mutein Fc-fusion protein-encoding nucleic acids operably linked to a promoter.

In another aspect, provided herein are host cells comprising the isolated nucleic acids encoding the above IL-2 muteins, IL-2 mutein Fc-fusion proteins, or anti-IL-2 antibodies. The host cell may be a prokaryotic cell, such as *E. coli*, or may be a eukaryotic cell, such as a mammalian cell. In certain embodiments, the host cell is a Chinese hamster ovary (CHO) cell line.

In another aspect, provided herein are methods of making a human IL-2 mutein. The methods comprising culturing a host cell under conditions in which a promoter operably linked to a human IL-2 mutein is expressed. Subsequently, the human IL-2 mutein is harvested from said culture. The IL-2 mutein may be harvested from the culture media and/or host cell lysates.

In another aspect, provided herein are methods of making a human IL-2 mutein Fc-fusion protein. The methods comprising culturing a host cell under conditions in which a promoter operably linked to a human IL-2 mutein Fc-fusion protein is expressed. Subsequently, the human IL-2 mutein Fc-fusion protein is harvested from said culture. The human IL-2 mutein Fc-fusion protein may be harvested from the culture media and/or host cell lysates.

In another aspect, provided herein are methods of making an anti-IL-2 antibody. The methods comprising culturing a host cell under conditions in which promoters operably linked to the heavy and light chains of an anti-IL-2 antibody are expressed. Subsequently, the anti-IL-2 antibody is harvested from said culture. The anti-IL-2 antibody may be harvested from the culture media and/or host cell lysates.

Pharmaceutical Compositions

In some embodiments, the invention provides a pharmaceutical composition comprising a therapeutically effective amount of an IL-2 mutein or anti-IL-2 antibody together with a pharmaceutically effective diluents, carrier, solubilizer, emulsifier, preservative, and/or adjuvant. In certain embodiments, the IL-2 mutein is within the context of an IL-2 mutein Fc-fusion protein. Pharmaceutical compositions of the invention include, but are not limited to, liquid, frozen, and lyophilized compositions.

Preferably, formulation materials are nontoxic to recipients at the dosages and concentrations employed. In specific embodiments, pharmaceutical compositions comprising a therapeutically effective amount of an IL-2 mutein containing therapeutic molecule, e.g, an IL-2 mutein Fc-fusion, are provided.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine, proline, or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, 11-2 mutein or anti-IL-2 antibody compositions may be prepared for storage by mixing the selected composition having the desired degree of purity with optional formulation agents (REMINGTON'S PHARMACEUTI- CAL SCIENCES, supra) in the form of a lyophilized cake or an aqueous solution. Further, in certain embodiments, the IL-2 mutein or anti-IL-2 antibody product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired IL-2 mutein or anti-IL-2 antibody composition in a pharmaceutically acceptable vehicle. A particularly suitable vehicle for parenteral injection is sterile distilled water in which the mutein or anti-IL-2 antibody composition is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the IL-2 mutein or anti-IL-2 antibody composition.

Additional pharmaceutical compositions will be evident to those skilled in the art, including formulations involving IL-2 mutein or anti-IL-2 antibody compositions in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Aspects of the invention includes self-buffering IL-2 mutein or anti-IL-2 antibody formulations, which can be used as pharmaceutical compositions, as described in international patent application WO 06138181A2 (PCT/US2006/022599), which is incorporated by reference in its entirety herein.

As discussed above, certain embodiments provide IL-2 mutein or anti-IL-2 antibody compositions, particularly pharmaceutical 11-2 mutein Fc-fusion proteins, that comprise, in addition to the IL-2 mutein or anti-IL-2 antibody composition, one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions," Pharm Biotechnol. 13: 159-75 (2002), each of which is herein incorporated by reference in its entirety, particularly in parts pertinent to excipients and processes of the same for self-buffering protein formulations in accordance with the current invention, especially as to protein pharmaceutical products and processes for veterinary and/or human medical uses.

Salts may be used in accordance with certain embodiments of the invention to, for example, adjust the ionic strength and/or the isotonicity of a formulation and/or to improve the solubility and/or physical stability of a protein or other ingredient of a composition in accordance with the invention.

As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as "chaotropic." Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in IL-2 mutein or anti-IL-2 antibody formulations in accordance with various embodiments of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred polyols of the invention in this regard. PEG is useful to stabilize proteins and as a cryoprotectant and can be used in the invention in this regard.

Embodiments of IL-2 mutein and/or anti-IL-2 antibody formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product.

Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188.

Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of IL-2 mutein or anti-IL-2 antibody formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard.

Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins.

Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+2}$ ions.

Embodiments of IL-2 mutein or anti-IL-2 antibody formulations further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin (liquid, Novo Nordisk), Nutropin AQ (liquid, Genentech) & Genotropin (lyophilized—dual chamber cartridge, Pharmacia & Upjohn) contain phenol while Somatrope (Eli Lilly) is formulated with m-cresol.

In one embodiment, an IL-2 mutein or Fc-fusion of an IL-2 mutein, such as, for example, any of the IL-2 muteins or Fc-fusion of an IL-2 mutein described herein, is formulated in 10 mM KPi, 161 mM L-arginine, at pH 7.6.

Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability.

In another aspect, the present invention provides IL-2 muteins or Fc-fusions of IL-2 muteins in lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (about 18 to 24 months). An important point to note is that preservative effectiveness should be demonstrated in the final formulation containing the active drug and all excipient components.

IL-2 mutein formulations generally will be designed for specific routes and methods of administration, for specific administration dosages and frequencies of administration, for specific treatments of specific diseases, with ranges of bio-availability and persistence, among other things. Formulations thus may be designed in accordance with the invention for delivery by any suitable route, including but not limited to orally, aurally, ophthalmically, rectally, and vaginally, and by parenteral routes, including intravenous and intraarterial injection, intramuscular injection, and subcutaneous injection.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of an IL-2 mutein pharmaceutical composition to be employed will depend, for example, upon the therapeutic context and objectives. One skilled in the art will appreciate that the appropriate dosage levels for treatment will vary depending, in part, upon the molecule delivered, the indication for which the IL-2 mutein or anti-IL-2 antibody is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 1 mg/kg or more, depending on the factors mentioned above. In specific embodiments, the dosage may range from 0.5 jag/kg up to about 100 µg/kg, optionally from 2.5 µg/kg up to about 50 µg/kg.

A therapeutic effective amount of an IL-2 mutein or anti-IL-2 antibody preferably results in a decrease in severity of disease symptoms, in an increase in frequency or duration of disease symptom-free periods, or in a prevention of impairment or disability due to the disease affliction.

Pharmaceutical compositions may be administered using a medical device. Examples of medical devices for administering pharmaceutical compositions are described in U.S. Pat. Nos. 4,475,196; 4,439,196; 4,447,224; 4,447,233; 4,486,194; 4,487,603; 4,596,556; 4,790,824; 4,941,880; 5,064,413; 5,312,335; 5,312,335; 5,383,851; and 5,399,163, all incorporated by reference herein.

In one embodiment, a pharmaceutical composition is provided comprising

Methods of Treating Autoimmune or Inflammatory Disorders

In certain embodiments, an IL-2 mutein or anti-IL-2 antibody of the invention is used to treat an autoimmune or inflammatory disorder. In preferred embodiments, an IL-2 mutein Fc-fusion protein is used.

Disorders that are particularly amenable to treatment with IL-2 mutein or anti-IL-2 antibody disclosed herein include, but are not limited to, inflammation, autoimmune disease, atopic diseases, paraneoplastic autoimmune diseases, cartilage inflammation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reiter's Syndrome, SEA Syndrome (Seronegativity, Enthesopathy, Arthropathy Syndrome), dermatomyositis, psoriatic arthritis, scleroderma, vasculitis, myolitis, polymyolitis, dermatomyolitis, polyarteritis nodossa, Wegener's granulomatosis, arteritis, ploymyalgia rheumatica, sarcoidosis, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, rhinosinusitis, rhinosinusitis with polyps, eosinophilic esophagitis, eosinophilic bronchitis, Guillain-Barre disease, Type I diabetes mellitus, thyroiditis (e.g., Graves' disease), Addison's disease, Raynaud's phenomenon, autoimmune hepatitis, GVHD, transplantation rejection, kidney damage, hepatitis C-induced vasculitis, spontaneous loss of pregnancy, and the like.

In preferred embodiments, the autoimmune or inflammatory disorder is lupus, graft-versus-host disease, hepatitis C-induced vasculitis, Type I diabetes, multiple sclerosis, spontaneous loss of pregnancy, atopic diseases, and inflammatory bowel diseases.

In another embodiment, a patient having or at risk for developing an autoimmune or inflammatory disorder is treated with an IL-2 mutein or anti-IL-2 antibody (for example, an IL-2 mutein disclosed herein, such as an IL-2 mutein Fc-fusion as disclosed herein, or another IL-2 mutein known in the art or wild-type IL-2, optionally as part of an Fc-fusion molecule of the type described herein) and the patient's response to the treatment is monitored. The patient's response that is monitored can be any detectable or measurable response of the patient to the treatment, or any combination of such responses. For example, the response can be a change in a physiological state of the patient, such as body temperature or fever, appetence, sweating, headache, nausea, fatigue, hunger, thirst, mental acuity, or the like. Alternatively, the response can be a change in the amount of a cell type or gene product (for example, a protein, peptide, or nucleic acid), for example, in a sample of peripheral blood taken from the patient. In one embodiment, the patient's treatment regimen is altered if the patient has a detectable or measurable response to the treatment, or if such response crosses a particular threshold. The alteration can be a reduction or increase in the frequency in dosing, or a reduction or increase in the amount of the IL-2 mutein or anti-IL-2 antibody administered per dose, or a "holiday" from dosing (i.e., a temporary cessation of treatment, either for a specified period of time, or until a treating physician determines that treatment should continue, or until a monitored response of the patient indicates that treatment should or can resume), or the termination of treatment. In one embodiment, the response is a change in the patient's temperature or CRP levels. For example, the response can be an increase in the patient's body temperature, or an increase of the CRP levels in a sample of peripheral blood, or both. In one particular embodiment, the patient's treatment is reduced, suspended, or terminated if the patient's body temperature increases during the course of treatment by at least 0.1°, 0.2°, 0.3°, 0.4°, 0.5°, 0.7°, 1°, 1.5°, 2°, or 2.5° C. In another particular embodiment, the patient's treatment is reduced, suspended, or terminated if the concentration of CRP in a sample of the patient's peripheral blood increases during the course of treatment by at least 0.1, 0.2, 0.3, 0.4, 0.5, 0.7, 1, 1.5, or 2 mg/mL. Other patient reactions that can be monitored and used in deciding whether to modify, reduce, suspend, or terminate treatment include the development or worsening of capillary leak syndrome (hypotension and cardiovascular instability), impaired neutrophil function (for example, resulting in or detected the development or worsening of an infection), thrombocytopenia, thrombotic angiopathy, injection site reactions, vasculitis (such as Hepatitis C virus vasculitis), or inflammatory symptoms or diseases. Further patient reactions that can be monitored and used in deciding whether to modify, reduce, increase, suspend, or terminate treatment include an increase in the number of NK cells, Treg cells, FOXP3$^-$ CD4 T cells, FOXP3$^+$CD4 T cells, FOXP3– CD8 T cells, or eosinophils. Increases of these cell types can be detected, for example, as an increase in the number of such cells per unit of peripheral blood (for example, expressed as an increase in cells per milliliter of blood) or as an increase in the percentage of such cell type compared to another type of cell or cells in the blood sample. Another patient reaction that can be monitored is an increase in the amount of cell surface-bound IL-2 mutein or anti-IL-2 antibody on CD25$^+$ cells in a sample of the patient's peripheral blood.

Methods of Expanding Treg Cells

The IL-2 mutein, anti-IL-2 antibody, or IL-2 mutein Fc-fusion protein may be used to expand Treg cells within a subject or sample. Provided herein are methods of increasing the ratio of Tregs to non-regulatory T cells. The method comprises contacting a population of T cells with an effective amount of a human IL-2 mutein, anti-IL-2 antibody or IL-2 mutein Fc-fusion. The ratio may be measured by determining the ratio of CD3+FOXP3+ cells to CD3+

FOXP3− cells within the population of T cells. The typical Treg frequency in human blood is 5-10% of total CD4+ CD3+ T cells, however, in the diseases listed above this percentage may be lower or higher. In preferred embodiments, the percentage of Treg increases at least 10%, at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, or at least 1000%. Maximal fold increases in Treg may vary for particular diseases; however, a maximal Treg frequency that might be obtained through IL-2 mutein treatment is 50% or 60% of total CD4+CD3+ T cells. In certain embodiments, the IL-2 mutein, anti-IL-2 antibody, or IL-2 mutein Fc-fusion protein is administered to a subject and the ratio of regulatory T cells (Tregs) to non-regulatory T cells within peripheral blood of a subject increases.

Because the IL-2 mutein, anti-IL-2 antibody, and IL-2 mutein Fc-fusion proteins preferentially expand Tregs over other cell types, they also are useful for increasing the ratio of regulatory T cells (Tregs) to natural killer (NK) cells within the peripheral blood of a subject. The ratio may be measured by determining the ratio of CD3+FOXP3+ cells to CD16+ and/or CD56+ lymphocytes that are CD19− and CD3−.

It is contemplated that the IL-2 mutein, anti-IL-2 antibody, or IL-2 mutein Fc-fusion protein may have a therapeutic effect on a disease or disorder within a patient without significantly expanding the ratio of Tregs to non-regulatory T cells or NK cells within the peripheral blood of the patient. The therapeutic effect may be due to localized activity of the IL-2 mutein, anti-IL-2 antibody, or IL-2 mutein Fc-fusion protein at the site of inflammation or autoimmunity.

EXAMPLES

The following examples, both actual and prophetic, are provided for the purpose of illustrating specific embodiments or features of the present invention and are not intended to limit its scope.

Example 1—pSTAT5 Signaling of IL-2 Muteins

IL-2 muteins were investigated for relative pSTAT5 activation. The activity screen was designed to identify muteins with enhanced Treg:Teff window, i.e., those that retained high level of activity in Treg cells while showing significant attenuation in Teff cells. Since activated Teff cells express increased levels of CD25, and patients with autoimmune and inflammatory diseases possess elevated number of these cells, we applied CD25+-gating on Teff cells to mimic the more realistic differentiation in CD25 expression in patients. The activity of IL-2 muteins was assessed by phosphor-STAT5 response in cells measured by FACS based assay. Briefly, previously frozen human PBMC was thawed and rested in complete media for 0.5-2 hrs. Cells were suspended at 5-10 million cells/ml and aliquoted at 100 ul per well in a 96-well deep well plate (0.5-1 million cells per well). Cells were stimulated with IL-2 muteins at 10× dose titration ranging from 1 nM to 200 nM at a final volume of 10 μl for 30 min. The level of STAT5 phosphorylation was measured using BD phosflow buffer kit. Briefly, 1 ml of BD lyse/fix phosflow buffer was added to stop stimulation. Cells were fixed for 10-15 min at 37° C. and permeabilized with 1×BD phosflow perm buffer on ice before being stained for CD3, CD4, CD25, FOXP3, CD8 and pSTAT5. The results for two donors of PBMC are shown in Table 2 below.

TABLE 2

| | pSTAT5 activation of IL-2 muteins | | | | | | | |
|---|---|---|---|---|---|---|---|---|
| | Donor 1 | | | | Donor 2 | | | |
| | 1 nM IL2 Treatment | | 200 nM IL2 Treatment | | 1 nM IL2 Treatment | | 200 nM IL2 Treatment | |
| IL2 | % pSTAT5 + Tregs | % pSTAT5 + Teffs | % pSTAT5 + Tregs | % pSTAT5 + Teffs | % pSTAT5 + Tregs | % pSTAT5 + Teffs | % pSTAT5 + Tregs | % pSTAT5 + Teffs |
| Media only | 1.86 | 0.655 | 2.57 | 0.68 | 0.29 | 1.24 | 0.59 | 0.4 |
| WTIL2 | 89.95 | 48.3 | 94.4 | 41 | 96.6 | 80.4 | 95.4 | 78.1 |
| N88D | | | 92.2 | 27 | 89.3 | 39.9 | 95.2 | 56 |
| V91R | 87.45 | 40.3 | 97.25 | 39.25 | | | | |
| H16R | 47.5 | 5.135 | 66.5 | 11.85 | 56.4 | 14.6 | 73.7 | 19.3 |
| N88R | 70.2 | 20.1 | 87.6 | 38.8 | 84.3 | 32.6 | 91.7 | 44.5 |
| V91H | 90.4 | 61.35 | 95.8 | 54.35 | 95.7 | 81.7 | 96.3 | 76.6 |
| N88K | 31.2 | 3.195 | 67.1 | 17.35 | 42 | 6.61 | 77.3 | 15.5 |
| D20W | 5.445 | 1.15 | 31.1 | 5.5 | 8.48 | 2.55 | 27.9 | 2.66 |
| D20A | 38.85 | 5.435 | 63.65 | 19.45 | 49 | 5.94 | 64 | 15 |
| H16E | 88.2 | 52.3 | 95.5 | 52.25 | 95.7 | 70.8 | 95.4 | 72 |
| E61Q | 88.65 | 68.05 | 95.4 | 67.3 | 96.3 | 84 | 96.5 | 83.2 |
| V91K, H16E | 41.45 | 5.425 | 60.25 | 15.55 | 53 | 10.1 | 67.9 | 15.3 |
| V91R, C125A | 88.95 | 50.45 | 95.7 | 51.7 | 95.7 | 76.6 | 96.2 | 75.7 |
| V91H, E61Q | 87.05 | 43.8 | 96.75 | 68.85 | 93 | 59.7 | 97.5 | 83.1 |
| V91K, H16R | 1.61 | 0.63 | 6.96 | 1.845 | 2.31 | 2.22 | 2.96 | 1.65 |
| V91K, D20W | 1.215 | 0.85 | 3.265 | 1.465 | 2.14 | 2.68 | 1.74 | 1.99 |
| V91K, D20A | 9.19 | 1.185 | 30.15 | 4.385 | 15.9 | 2.43 | 30.8 | 5.79 |
| V91K, N88K | 1.69 | 0.64 | 6.87 | 1.075 | 2.01 | 1.65 | 2.68 | 0.91 |
| H16E, V91H | 78.45 | 24.75 | 88.1 | 36.55 | 89.6 | 42.2 | 92.1 | 48.7 |
| V91H, D20A | 7.15 | 0.805 | 24.55 | 3.11 | 11.1 | 1.83 | 22.5 | 4.32 |
| H16R, D20A | 1.205 | 1.13 | 4.27 | 0.93 | 2.19 | 1.45 | 0.86 | 1.89 |
| D20A, H16E | 19.85 | 1.66 | 39.3 | 5.945 | 28.6 | 3.67 | 39 | 5.3 |
| V91H, H16R | 14.35 | 1.35 | 35.1 | 4.55 | 24.5 | 3.3 | 36.1 | 4.8 |
| H16E, N88K | 1.475 | 0.495 | 3.14 | 0.625 | 1.09 | 1.09 | 0.8 | 0 |
| D20A, E61Q | 10.13 | 1.005 | 65.95 | 20.1 | 9.72 | 1.82 | 68.9 | 16.3 |
| H16E, E61Q | 64.95 | 12.05 | 95.45 | 61.35 | 70.6 | 10.2 | 96 | 75.5 |

TABLE 2-continued

| | | | | | | | | |
|---|---|---|---|---|---|---|---|---|
| | pSTAT5 activation of IL-2 muteins | | | | | | | |
| | Donor 1 | | | | Donor 2 | | | |
| | 1 nM IL2 Treatment | | 200 nM IL2 Treatment | | 1 nM IL2 Treatment | | 200 nM IL2 Treatment | |
| IL2 | % pSTAT5 + Tregs | % pSTAT5 + Teffs | % pSTAT5 + Tregs | % pSTAT5 + Teffs | % pSTAT5 + Tregs | % pSTAT5 + Teffs | % pSTAT5 + Tregs | % pSTAT5 + Teffs |
| V91K, E61Q | 69.5 | 14.3 | 95.4 | 57.05 | 73.7 | 12.1 | 96.6 | 74.1 |
| V91K, E61Q, H16E | 6.02 | 1.135 | 52.5 | 11.7 | 6.21 | 1.15 | 58.6 | 10.5 |
| V91K, E61Q, H16R | 3.075 | 1.435 | 8.52 | 1.155 | 1.87 | 0.65 | 3.74 | 1.68 |
| V91K, E61Q, D20A | 2.215 | 0.88 | 26.6 | 2.71 | 1.84 | 0.98 | 22.5 | 2.51 |
| D20A, H16E, E61Q | 2.715 | 0.775 | 32.25 | 3.325 | 1.49 | 0.81 | 27.6 | 3.73 |
| D20A, H16R, E61Q | 15.35 | 1.465 | 80.9 | 27.65 | 13.3 | 1.88 | 86 | 29.9 |
| V91H, H16R, E61Q | 76.85 | 24.6 | 95.1 | 44.3 | 82.5 | 24.7 | 95.4 | 68.3 |
| H16E, V91H, E61Q | 24.4 | 1.235 | 83.4 | 33.55 | 26.7 | 2.04 | 90.9 | 44.1 |
| V91H, D20A, E61Q | 16.8 | 1.3 | 94.1 | 51.6 | 19 | 2.54 | 95.3 | 64.2 |
| N88K, M104T | 2.2 | 0.71 | 11.035 | 0.98 | 3.6 | 1.06 | 9.22 | 1.47 |
| V91H, M104T | 89.35 | 47.65 | 97.65 | 44.6 | 96.9 | 77.5 | 97.1 | 69.5 |
| D20A, M104T | 52.7 | 7.195 | 70.3 | 17.1 | 67 | 12.3 | 78.3 | 19.8 |
| H16E, M104T | 88.15 | 47.7 | 96.25 | 44 | 95.9 | 71.7 | 95.9 | 63.3 |
| N88K, M104V | 4.89 | 1.025 | 21 | 1.655 | 4.26 | 0.91 | 17.7 | 2.72 |
| V91H, M104V | 89.35 | 50.8 | 97 | 50.9 | 95.2 | 73.1 | 96.7 | 71.7 |
| D20A, M104V | 52.55 | 6.245 | 70.05 | 16.2 | 66.7 | 12 | 76.2 | 18.9 |
| H16E, M104V | 88.95 | 47.4 | 96.25 | 44.2 | 91.1 | 59.8 | 96.5 | 67.5 |
| V91K, H16E, M104T | 44.45 | 4.105 | 62.7 | 11.175 | 54.7 | 7.07 | 70.7 | 17.2 |
| V91K, H16R, M104T | 1.92 | 1.16 | 10.9 | 2.3 | 3.22 | 1.64 | 5.64 | 1.65 |
| V91K, D20A, M104T | 9.34 | 0.9 | 31.05 | 4.78 | 18.5 | 2.52 | 28.9 | 1.59 |
| D20A, H16E, M104T | 22.25 | 1.94 | 42 | 8.835 | 34.2 | 2.33 | 46 | 9.92 |
| H16E, V91H, M104T | 78.6 | 24.6 | 89.05 | 37.75 | 91 | 35.2 | 93.2 | 46.7 |
| V91H, D20A, M104T | 8.825 | 1.105 | 27.1 | 4.355 | 15.3 | 1.9 | 21.7 | 3.48 |
| V91K, H16E, M104V | 39.15 | 4.94 | 57.5 | 13.1 | 56.6 | 9.66 | 66.7 | 11.7 |
| V91K, H16R, M104V | 2.175 | 1.06 | 8.995 | 1.74 | 4.09 | 1.5 | 3.98 | 0.7 |
| V91K, D20A, M104V | 9.07 | 1.275 | 30.2 | 4.165 | 21.3 | 2.74 | 34.8 | 4.81 |
| H16E, V91H, M104V | 79.3 | 22.7 | 86.3 | 33.4 | 90.3 | 36.8 | 92.3 | 50.4 |
| V91H, D20A, M104V | 7.985 | 1.365 | 25.6 | 3.78 | 11.2 | 2.96 | 21.1 | 2.6 |
| V91K, H16E, E61Q, M104T | 35.25 | 3.21 | 88.1 | 35.95 | 37.6 | 4.74 | 93.4 | 45.4 |
| V91K, H16R, E61Q, M104T | 1.57 | 0.81 | 13.8 | 1.4 | 1.68 | 0.74 | 6.93 | 1.27 |
| H16E, V91H, E61Q, M104T | 25.8 | 1.925 | 84.1 | 39.8 | 38.9 | 2.63 | 91.9 | 47.7 |
| V91H, D20A, E61Q, M104T | 49.5 | 6.74 | 71.2 | 18.2 | 67.4 | 11.3 | 79.5 | 22.9 |
| D20W, E61Q | 2.29 | 0.77 | 6.655 | 1.34 | 2.45 | 1.2 | 2.97 | 1 |
| D20W, V91K, E61Q | 3.855 | 1.1 | 36.3 | 4.41 | 2.89 | 1.15 | 32.5 | 4.57 |
| N88K, E61Q | 18.2 | 1.64 | 92.95 | 45.7 | 26.7 | 4.22 | 97.1 | 64.1 |
| V91K, N88K, E61Q | 5.42 | 0.485 | 83.25 | 30.15 | 6.34 | 1.45 | 91.5 | 41.5 |
| V91K, N88K, E61Q, M104T | 2.9 | 0.765 | 76.2 | 21.4 | 4.02 | 1.35 | 87.7 | 29.6 |
| D20W, V91K, E61Q, M104T | 80.6 | 27.05 | 95.2 | 41.25 | 89.2 | 35.7 | 97 | 61.5 |
| V91H, M104L | 90.55 | 47.85 | 96.85 | 39.65 | 98.1 | 63.9 | 96.9 | 66.3 |
| D20A, M104L | 47.7 | 5.28 | 69.2 | 15.35 | 66 | 12.6 | 76.7 | 24.4 |
| H16E, M104L | 89.25 | 43.45 | 95.6 | 38.75 | 97.2 | 61 | 96.6 | 62.1 |
| V91K, H16R, M104L | 3.4 | 1.04 | 10.265 | 0.785 | 5.19 | 2.74 | 5.93 | 1.64 |
| V91K, D20A, M104L | 11.95 | 1.47 | 30.55 | 3.665 | 21 | 2.89 | 30.5 | 4.89 |

Example 2—Stability of IL-2 Muteins

Molecule assessment assays of DSC Tm measurement along with 40° C. 10 day stability measured by SEC chromatography was tested for selection of stable molecules with good manufacturability potential. The results of % MP following 10 days are shown in FIG. 1.

Example 3—Attenuation of Human IL-2 Muteins

Figure 2:
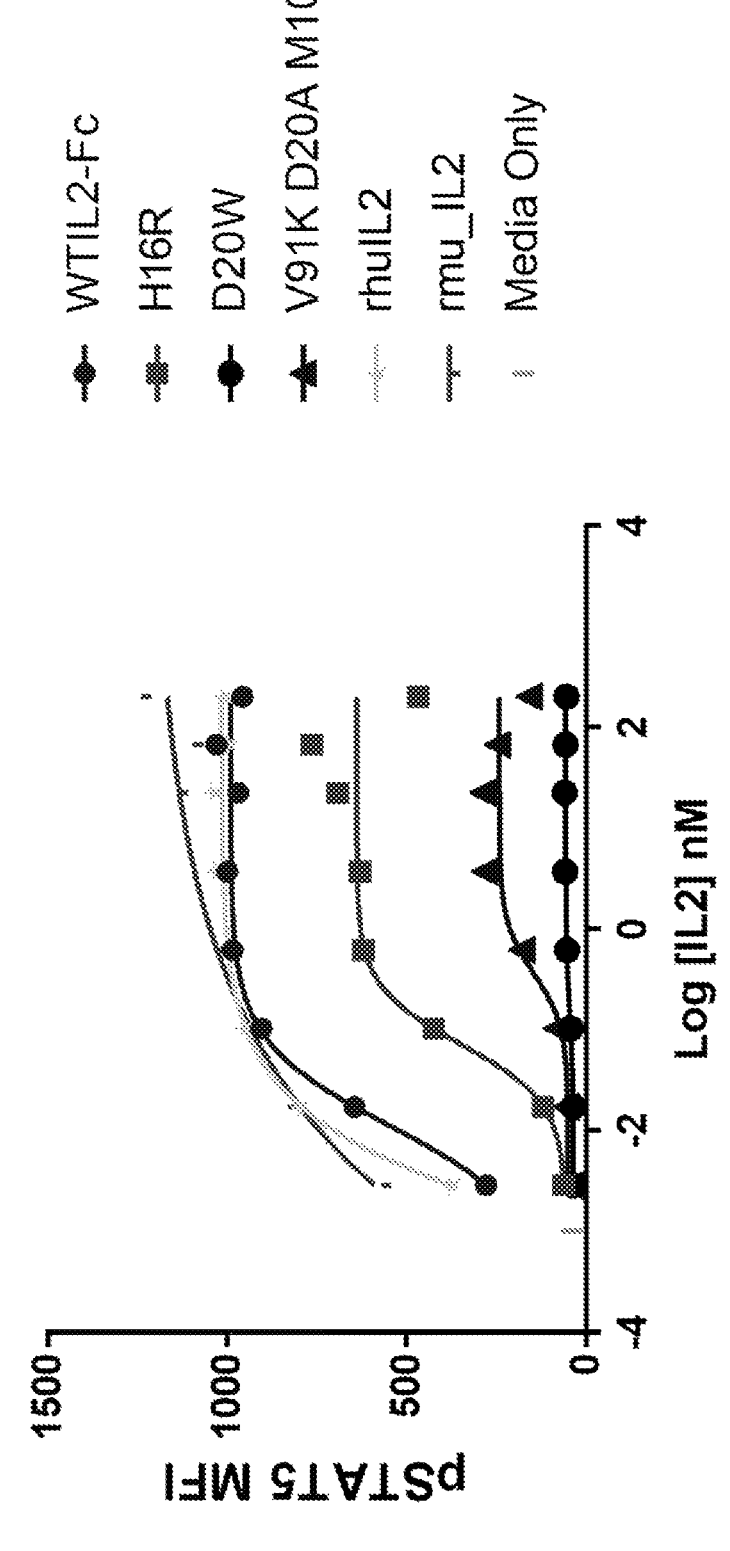
FIG. 2 shows dose titration curves for three attenuated muteins, H16R, V91K D20A M104V, D20W, and controls, wildtype human IL-2.Fc, recombinant human IL-2, and recombinant mouse IL-2 in an in vitro pSTAT5 assay.

Attenuated human IL-2 muteins were evaluated for activity in mouse splenocytes in an in vitro pSTAT5 assay. We confirmed the activity of the selected muteins on mouse immune cells in a mouse splenocyte pSTAT5 assay (FIG. 2). Shown are dose titration curves for three attenuated muteins, H16R, V91K D20A M104V, D20W, and controls, wildtype human IL-2.Fc, recombinant human IL-2, and recombinant mouse IL-2. Mouse splenocytes were stimulated for 30 min in media containing titrating concentrations of the muteins and analyzed by FACS. The muteins demonstrated similar rank order of activity in mouse Treg cells as did they in human Treg cells (i.e., WT>H16R>V91K D20A M104V>D20W). The rank order was similar for T effector cells as well.

Example 4—In Vivo Activity of Human IL-2 Muteins in Mice

Figure 3:
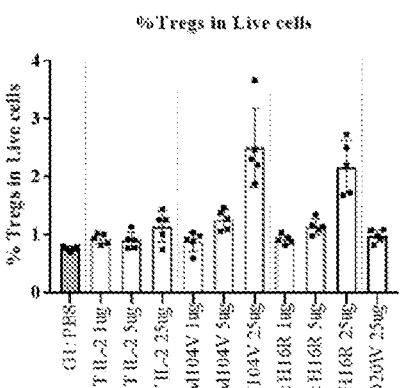
FIG. 3 shows evaluation of human IL-2 muteins V91K D20A M104V, H16R, D20W, and control wildtype IL-2-Fc for in vivo activity in mice.
Figure 3:
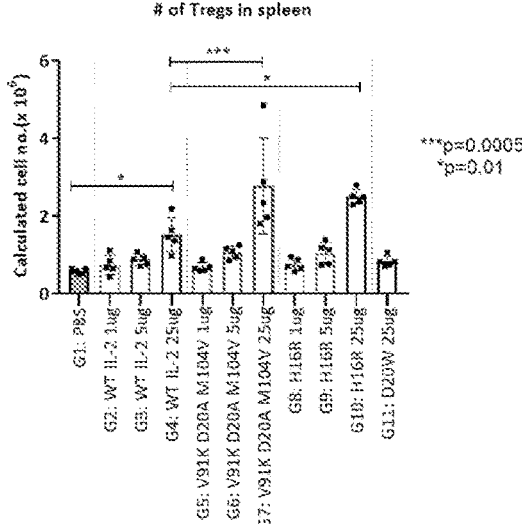
Figure 3:
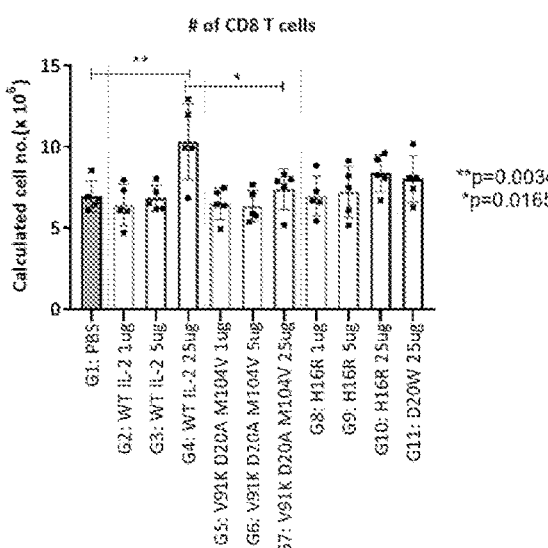
Figure 3:
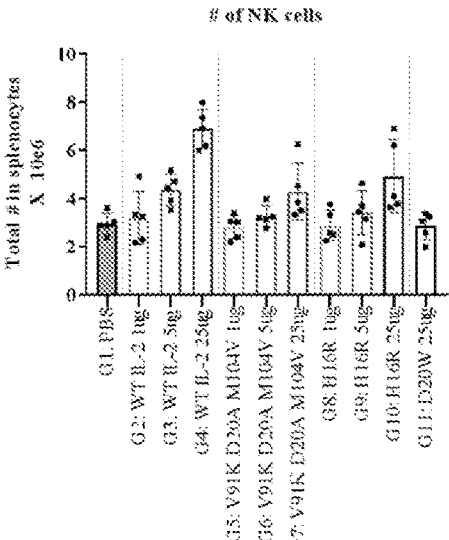

C57Bl6 mice were given a single dose of PBS (vehicle control), wildtype IL-2-Fc, V91K D20A M104V, H16R, or D20W on day 0, and splenocytes were harvested and analyzed on day 4 for effects on Treg cells, CD8 T and NK cells. Three doses (1 ug, 5 ug, or 25 ug per mouse) were evaluated, except D20W which was given at 25 ug only. The percentage of Treg cells, as defined by CD4+CD25+FoxP3+ cells, in total live gated cells are shown in (A), and calculated total numbers of Treg cells (B), CD8 T cells (C), and NK cells (D) are shown. As illustrated in FIG. 3, wildtype IL-2, H16R, and V91K D20A M104V induced significant expansion of Treg cells in vivo in a dose-dependent manner. The two muteins, H16R and V91K D20A M104V, showed surprisingly robust activity on Treg cells, to a similar or even greater extent than the wildtype IL-2.Fc. In contrast, neither H16R nor V91K D20A M104V demonstrated significant activity on CD8 T or NK cells compared to wildtype IL-2.Fc. These results demonstrate that, despite significant attenuation of activity as measured by pSTAT5 readout in vitro, attenuated muteins retain the ability to induce robust Treg response in vivo, while inducing minimal CD8 T and NK cell response. Thus, attenuation disproportionately impacts Treg:non-Treg selectivity in vivo.

Example 5—pSTAT5 Signaling of IL-2 Muteins

IL-2 muteins were investigated for relative pSTAT5 activation. The activity screen was designed to identify muteins with enhanced Treg:Teff window, i.e., those that retained high level of activity in Treg cells while showing significant attenuation in Teff cells. Since activated Teff cells express increased levels of CD25, and patients with autoimmune and inflammatory diseases possess elevated number of these cells, we applied CD25+-gating on Teff cells to mimic the more realistic differentiation in CD25 expression in patients. The activity of IL-2 muteins was assessed by phosphor-STAT5 response in cells measured by FACS based assay. Briefly, previously frozen human PBMC was thawed and rested in complete media for 0.5-2 hrs. Cells were suspended at 5-10 million cells/ml and aliquoted at 100 ul per well in a 96-well deep well plate (0.5-1 million cells per well). Cells were stimulated with IL-2 muteins at 10× dose titration ranging from 0.4 nM to 25 nM at a final volume of 10 μl for 30 min. The level of STAT5 phosphorylation was measured using BD phosflow buffer kit. Briefly, 1 ml of BD lyse/fix phosflow buffer was added to stop stimulation. Cells were fixed for 10-15 min at 37° C. and permeabilized with 1×BD phosflow perm buffer on ice before being stained for CD3, CD4, CD25, FOXP3, CD8 and pSTAT5. The results for two donors of PBMC are shown in Table 2 below.

TABLE 3

| | pSTAT5 activation of IL-2 muteins | | | | | | | |
|---|---|---|---|---|---|---|---|---|
| | Donor 1 | | | | Donor 2 | | | |
| | 25 nM IL2 Treatment | | 0.4 nM IL2 Treatment | | 25 nM IL2 Treatment | | 0.4 nM IL2 Treatment | |
| IL2 | % pSTAT5 + Tregs | % pSTAT5 + Teffs | % pSTAT5 + Tregs | % pSTAT5 + Teffs | % pSTAT5 + Tregs | % pSTAT5 + Teffs | % pSTAT5 + Tregs | % pSTAT5 + Teffs |
| Media only | 3.85 | .045 | | | | | | |
| WTIL2 | 100 | 87.7 | 99.7 | 85.3 | 99.8 | 91.9 | 99.5 | 90.3 |
| V91A, H16A | 99.7 | 89 | 99.8 | 85.8 | 99.8 | 91.4 | 99.2 | 43.4 |
| V91A, H16D | 99.4 | 82.9 | 99.7 | 76.4 | 100 | 84.5 | 95.1 | 22 |
| V91A, H16E | 99.6 | 76.7 | 100 | 63.6 | 99.6 | 69.4 | 84.4 | 11 |
| V91A, H16S | 99.9 | 84.1 | 99.8 | 80.9 | 99.7 | 88.6 | 99.1 | 38.1 |
| V91E, H16A | 99.6 | 85 | 99.8 | 78.1 | 99.8 | 87.5 | 96.4 | 28.3 |
| V91E, H16D | 99.5 | 72.6 | 99.2 | 56.9 | 99.8 | 64.7 | 81.2 | 11.2 |
| V91E, H16E | 99.3 | 63.3 | 99.3 | 48.1 | 99 | 62.3 | 74.3 | 7.16 |
| V91E, H16S | 100 | 84.2 | 99.3 | 76.1 | 99.8 | 87.3 | 96.6 | 28.3 |
| V91K, H16A | 99.3 | 73.4 | 98.9 | 55.9 | 100 | 65.6 | 82.4 | 12.6 |
| V91K, H16D | 96.1 | 37.5 | 93.8 | 22.8 | 95.4 | 30 | 45.1 | 2.1 |
| V91K, H16S | 99.4 | 71 | 99 | 53.3 | 99.8 | 68.5 | 70.7 | 3.36 |
| V91S, H16E | 98.6 | 60.1 | 98.9 | 45 | 98.9 | 53.6 | 70.5 | 7.58 |

What is claimed is:

1. A human interleukin-2 (IL-2) mutein comprising an amino acid sequence that is at least 97% identical to the amino acid sequence set forth in SEQ ID NO: 2, wherein said IL-2 mutein has the V91K and H16E mutations; and wherein said IL-2 mutein preferentially stimulates T regulatory cells relative to other T cells.

2. The human IL-2 mutein of claim 1, wherein the IL-2 mutein further preferentially stimulates T regulatory cells relative to natural killer (NK) cells.

3. The human IL-2 mutein of claim 1, wherein the amino acid sequence of said mutein further comprises the C125A mutation.

4. The human IL-2 mutein of claim 1, wherein the IL-2 mutein has less than 30% phosphorylated Signal Transducer and Activator of Transcription 5 (pSTAT5) activation of T effector cells at 1 nM IL-2 treatment, using a fluorescence-activated cell sorting (FACS)-based peripheral blood mononuclear cell (PBMC) assay.

5. The human IL-2 mutein of claim 1, wherein the IL-2 mutein has less than 30% pSTAT activation of T effector cells and greater than 40% pSTAT activation of T regulatory cells at 1 nM IL-2 treatment, using a FACS-based PBMC assay.

6. The human IL-2 mutein of claim 1, wherein the IL-2 mutein has greater than 40% pSTAT activation of T regulatory cells at 1 nM IL-2 treatment, using a FACS-based PBMC assay.

7. The human IL-2 mutein of claim 1, further wherein the IL-2 mutein has greater than 30% stability at 40° C. after 10 days.

8. An fragment crystallizable (Fc)-fusion protein comprising an Fc and the human IL-2 mutein of claim 1.

9. The Fc-fusion protein of claim 8, wherein the Fc is a human IgG1 Fc, wherein the human IgG1 Fc comprises one or more mutations altering effector function of said Fc.

10. The Fc-fusion protein of claim 9, comprising a substitution or deletion of the C-terminal lysine of said human IgG Fc.

11. The Fc-fusion protein of claim 9, wherein a linker connects the Fc and human IL-2 mutein portions of said protein.

12. The Fc-fusion protein of claim 11, wherein the linker is GGGGS (SEQ ID NO: 5), GGNGT (SEQ ID NO: 6), or YGNGT (SEQ ID NO: 7).

13. The Fc-fusion protein of claim 9, wherein the IL-2 mutein further comprises an amino acid addition, substitution, or deletion altering glycosylation of said Fc-fusion protein when expressed in mammalian cells.

14. The Fc-fusion protein of claim 9, wherein said Fc-fusion protein comprises an Fc dimer.

15. The Fc-fusion protein of claim 14, wherein said Fc-fusion protein comprises two IL-2 muteins.

16. The Fc-fusion protein of claim 14, wherein said Fc-fusion protein comprises a single IL-2 mutein.

17. An isolated nucleic acid encoding the Fc fusion protein of claim 8.

18. A method of increasing the ratio of regulatory T cells (Tregs) to non-regulatory T cells within a population of T cells or within peripheral blood of a subject in need thereof, comprising contacting the population of T cells with an effective amount of an Fc-fusion protein of claim 8.

19. A method of increasing the ratio of regulatory T cells (Tregs) to natural killer (NK) cells within the peripheral blood of a subject in need thereof, comprising administering an effective amount of an Fc-fusion protein of claim 8.

20. A method of treating a subject with an inflammatory or autoimmune disease, said method comprising administering to said subject a therapeutically effective amount of an Fc-fusion protein of claim 8.

21. An isolated nucleic acid encoding the human IL-2 mutein of claim 1.

22. A method of increasing the ratio of regulatory T cells (Tregs) to non-regulatory T cells within a population of T cells or within peripheral blood of a subject in need thereof, comprising contacting the population of T cells with an effective amount of a human IL-2 mutein of claim 1.

23. A method of increasing the ratio of regulatory T cells (Tregs) to natural killer (NK) cells within the peripheral blood of a subject in need thereof, comprising administering an effective amount of a human IL-2 mutein of claim 1.

24. A method of treating a subject with an inflammatory or autoimmune disease, said method comprising administering to said subject a therapeutically effective amount of an IL-2 mutein of claim 1.

25. The method of claim 24, wherein the inflammatory or autoimmune disease is lupus, graft-versus-host disease, hepatitis C-induced vasculitis, type I diabetes, type II diabetes, multiple sclerosis, rheumatoid arthritis, alopecia areata, atherosclerosis, psoriasis, organ transplant rejection, Sjögren's Syndrome, Behcet's disease, spontaneous loss of pregnancy, atopic diseases, asthma, or inflammatory bowel diseases.

* * * * *

SEQUENCE LISTING

<160> NUMBER OF SEQ ID NOS: 8

<210> SEQ ID NO 1
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (125)..(125)
<223> OTHER INFORMATION: Cys, Ser, Val or Ala

<400> SEQUENCE: 1

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Lys Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Xaa Gln Ser Ile
            115                 120                 125

Ile Ser Thr Leu Thr
    130
```

```
<210> SEQ ID NO 2
<211> LENGTH: 133
<212> TYPE: PRT
<213> ORGANISM: Homo sapiens
<220> FEATURE:
<221> NAME/KEY: MOD_RES
<222> LOCATION: (125)..(125)
<223> OTHER INFORMATION: Cys, Ser, Val or Ala

<400> SEQUENCE: 2
```

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Xaa Gln Ser Ile
            115                 120                 125

Ile Ser Thr Leu Thr
    130
```

```
<210> SEQ ID NO 3
<211> LENGTH: 227
<212> TYPE: PRT
<213> ORGANISM: Homo sapiens

<400> SEQUENCE: 3
```

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30
```

```
Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Arg Glu Glu Gln Tyr Asn Ser Thr Tyr
65              70              75              80

Arg Val Val Ser Val Leu Thr Val Leu His Gln Asp Trp Leu Asn Gly
                85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
            115             120             125

Tyr Thr Leu Pro Pro Ser Arg Glu Glu Met Thr Lys Asn Gln Val Ser
    130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
                165             170             175

Val Leu Asp Ser Asp Gly Ser Phe Phe Leu Tyr Ser Lys Leu Thr Val
                180             185             190

Asp Lys Ser Arg Trp Gln Gln Gly Asn Val Phe Ser Cys Ser Val Met
            195             200             205

His Glu Ala Leu His Asn His Tyr Thr Gln Lys Ser Leu Ser Leu Ser
    210             215             220

Pro Gly Lys
225

<210> SEQ ID NO 4
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Lys Thr His Thr Cys Pro Pro Cys Pro Ala Pro Glu Leu Leu Gly
1               5               10              15

Gly Pro Ser Val Phe Leu Phe Pro Pro Lys Pro Lys Asp Thr Leu Met
            20              25              30

Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Arg Glu Glu Gln Tyr Gly Ser Thr Tyr
65              70              75              80

Arg Val Val Ser Val Leu Thr Val Leu His Gln Asp Trp Leu Asn Gly
                85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
            115             120             125

Tyr Thr Leu Pro Pro Ser Arg Glu Glu Met Thr Lys Asn Gln Val Ser
    130             135             140

Leu Thr Cys Leu Val Lys Gly Phe Tyr Pro Ser Asp Ile Ala Val Glu
```

-continued

```
145               150              155              160

Trp Glu Ser Asn Gly Gln Pro Glu Asn Asn Tyr Lys Thr Thr Pro Pro
                165              170              175

Val Leu Asp Ser Asp Gly Ser Phe Phe Leu Tyr Ser Lys Leu Thr Val
            180              185              190

Asp Lys Ser Arg Trp Gln Gln Gly Asn Val Phe Ser Cys Ser Val Met
        195              200              205

His Glu Ala Leu His Asn His Tyr Thr Gln Lys Ser Leu Ser Leu Ser
    210              215              220

Pro Gly
225

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Asn Gly Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Gly Asn Gly Thr
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 8

His His His His His His
1               5
```